US005948638A

United States Patent [19]
Lin et al.

[11] Patent Number: 5,948,638
[45] Date of Patent: *Sep. 7, 1999

[54] TNF RECEPTOR DEATH DOMAIN LIGAND PROTEINS

[75] Inventors: Lih-Ling Lin, Concord; Jennifer Chen, Chestnut Hill; Andrea R. Schievella, Winchester; James Graham, Somerville, all of Mass.

[73] Assignee: Genetics Institute, Inc., Cambridge, Mass.

[*] Notice: This patent is subject to a terminal disclaimer.

[21] Appl. No.: 08/839,031

[22] Filed: Apr. 23, 1997

Related U.S. Application Data

[60] Division of application No. 08/533,901, Sep. 26, 1995, Pat. No. 5,852,173, which is a continuation-in-part of application No. 08/494,440, Jun. 19, 1995, Pat. No. 5,849,501, which is a continuation-in-part of application No. 08/327,514, Oct. 19, 1994, abandoned.

[51] Int. Cl.$^6$ .............................. C12N 15/12; C12N 5/10; C12N 15/10; C07K 14/47
[52] U.S. Cl. ....................... 435/69.1; 536/23.1; 536/23.5; 435/320.1; 435/325; 435/252.3; 435/254.11; 530/350; 530/351
[58] Field of Search ...................................... 530/350, 351, 530/388.22, 388.23; 536/23.1, 23.5; 435/69.1, 320.1, 325, 252.3, 254.11

[56] References Cited

U.S. PATENT DOCUMENTS

| | | | |
|---|---|---|---|
| 5,296,592 | 3/1994 | Dower et al. | 530/413 |
| 5,464,938 | 11/1995 | Smith | 530/350 |
| 5,506,340 | 4/1996 | Heavner | 530/324 |
| 5,563,039 | 10/1996 | Goeddel et al. | 435/7.1 |

FOREIGN PATENT DOCUMENTS

| | | |
|---|---|---|
| A-46127/93 | 9/1993 | Australia . |
| 308378 | 3/1989 | European Pat. Off. . |
| 433900 | 6/1991 | European Pat. Off. . |
| 526905 | 2/1993 | European Pat. Off. . |
| 0 585 939 A2 | 9/1993 | European Pat. Off. . |
| WO 92/03470 | 3/1992 | WIPO . |
| WO 92/03471 | 3/1992 | WIPO . |
| WO 92/14834 | 9/1992 | WIPO . |
| WO 93/19777 | 10/1993 | WIPO . |
| WO 94/01548 | 1/1994 | WIPO . |
| WO 94/10207 | 5/1994 | WIPO . |
| WO 95/31544 | 11/1995 | WIPO . |
| WO 95/33051 | 12/1995 | WIPO . |
| 96/25941 | 8/1996 | WIPO . |
| 96/34095 | 10/1996 | WIPO . |

OTHER PUBLICATIONS

Luban and Goff, 1995, Curr. Opin. Biotech. 6: 59–64.
GenBank Accession Number Z42819, accessed Jun. 4, 1998, Sep. 21, 1995.
Waye et al., Protein Engineering 8:90 (1995).
Auffray et al., Life Sciences 318:263–272 (1995).
Rothe et al., Cell 78:681–692 (1994).
Song et al., The Journal of Biological Chemistry 269:22492–22495 (1994).
Tartaglia et al., Cell 74:845–853 (1993).
Boldin et al., The Journal of Biological Chemistry 270(1):387–391 (1995).
Hsu et al., Cell 81:495–504 (1995).
Boldin et al., FEBS Letters 367:39–44 (1995).
Schall et al., Cell 61:361–370 (1990).
Shimasaki et al., J. Biol. Chem. 266:10646–10653 (1991).
Saragovi et al., Bio/Technology 10:773–778 (1992).
McDowell et al., J. Amer. Chem. Soc. 114:9245–9253 (1992).
Kaufman et al., Nucleic Acids Res. 19:4485–4490 (1991).
Kaufman et al., Methods in Enzymology 185:537–566 (1990).
Gyuris et al., Cell 75:791–803 (1993).
Gietz et al., Nucleic Acids Res. 20:1425 (1992).
Genbank accession No. U44953 (Jul. 1, 1996).
Genbank accession No. U48254 (Aug. 3, 1996).
Miki et al. (1992) Cancer Res. 52:643.
Darnay et al. (1994) J. Biol. Chem. 269:20299.
Kiefer et al. (1992) J. Biol. Chem. 267:12692.
Genbank accession No. T08593 (1993).
Genbank accession No. T07800 (1993).
Genbank accession No. M78050 (1992).
Genbank accession No. M78539 (1992).
Tartaglia et al, Tumor necrosis factor receptor signaling, J. Biol. Chem., 267(7):4304–4307.
Tartaglia et al., Tumor necrosis factor's cytoxic activity is signalled by the p55 TNF receptor, Cell, 73:213–216.

*Primary Examiner*—Lila Feisee
*Assistant Examiner*—Claire M. Kaufman
*Attorney, Agent, or Firm*—Suzanne A. Sprunger; Scott A. Brown

[57] ABSTRACT

Novel TNF receptor death domain ("TNF-R1-DD") ligand proteins are disclosed. Polynucleotides encoding the TNF-R1-DD ligand protein are also disclosed, along with vectors, host cells, and methods of making the TNF-R1-DD ligand protein. Pharmaceutical compositions containing the TNF-R1-DD ligand protein, methods of treating inflammatory conditions, and methods of inhibiting TNF-R death domain binding are also disclosed. Methods of identifying inhibitors of TNF-R death domain binding and inhibitors identified by such methods are also disclosed.

13 Claims, 8 Drawing Sheets

TNF RECEPTOR DEATH DOMAIN LIGAND PROTEINS

This application is a divisional of application Ser. No. 08/533,901, now U.S. Pat. No. 5,852,173, filed Sep. 26, 1995, which was a continuation-in-part of application Ser. No. 08/494,440, now U.S. Pat. No. 5,849,501, filed Jun. 19, 1995, which was a continuation-in-part of application Ser. No. 08/327,514, filed Oct. 19, 1994, now abandoned.

BACKGROUND OF THE INVENTION

The present invention relates to the field of anti-inflammatory substances and other substances which act by inhibiting binding to the intracellular domain of a tumor necrosis factor receptor (hereinafter "TNF-R"), such as, for example, the P55 type (or TNF-R1) TNF receptor. More particularly, the present invention is directed to novel ligands which bind to the TNF-R intracellular domain and to inhibition or modulation of signal transduction by this receptor.

Tumor necrosis factor (herein "TNF") is a cytokine which produces a wide range of cellular activities. TNF causes an inflammatory response, which can be beneficial, such as in mounting an immune response to a pathogen, or when overexpressed can lead to other detrimental effects of inflammation.

The cellular effects of TNF are initiated by the binding of TNF to its receptors (TNF-Rs) on the surface of target cells. The isolation of polynucleotides encoding TNF-Rs and variant forms of such receptors has been described in European patent publication Nos. EP 308,378, EP 393,438, EP 433,900, EP 526,905 and EP 568,925; in PCT patent publication Nos. WO91/03553 and WO93/19777; and by Schall et al., Cell 61:361–370 (1990) (disclosing the P55 type TNF receptor). Processes for purification of TNF-Rs have also been disclosed in U.S. Pat. No. 5,296,592.

Native TNF-Rs are characterized by distinct extracellular, transmembrane and intracellular domains. The primary purpose of the extracellular domain is to present a binding site for TNF on the outside of the cell. When TNF is bound to the binding site, a "signal" is transmitted to the inside of the cell through the transmembrane and intracellular domains, indicating that binding has occurred. Transmission or "transduction" of the signal to the inside of the cell occurs by a change in conformation of the transmembrane and/or intracellular domains of the receptor. This signal is "received" by the binding of proteins and other-molecules to the intracellular domain of the receptor, resulting in the effects seen upon TNF stimulation. Two distinct TNF receptors of ~55 kd ("TNF-R1") and ~75 kd ("TNF-R2") have been identified. Numerous studies with anti-TNF receptor antibodies have demonstrated that TNF-R1 is the receptor which signals the majority of the pleiotropic activities of TNF. Recently, the domain required for signaling cytotoxicity and other TNF-mediated responses has been mapped to the ~80 amino acid near the C-terminus of TNF-R1. This domain is therefore termed the "death domain" (hereinafter referred to as "TNF-R death domain" and "TNF-R1-DD") (see, Tartaglia el al., Cell 74:845–853 (1993)).

While TNF binding by TNF-Rs results in beneficial cellular effects, it is often desirable to prevent or deter TNF binding from causing other detrimental cellular effects. Although substantial effort has been expended investigating inhibition of TNF binding to the extracellular domain of TNF-Rs, examination of binding of proteins and other molecules to the intracellular domain of TNF-Rs has received much less attention.

However, ligands which bind to the TNF-R intracellular domain have yet to be identified. It would be desirable to identify and isolate such ligands to examine their effects upon TNF-R signal transduction and their use as therapeutic agents for treatment of TNF-induced conditions. Furthermore, identification of such ligands would provide a means for screening for inhibitors of TNF-R/intracellular ligand binding, which will also be useful as anti-inflammatory agents.

SUMMARY OF THE INVENTION

Applicants have for the first time identified novel TNF-R1-DD ligand proteins and have isolated polynucleotides encoding such ligands. Applicants have also identified a known protein which may also bind to the death domain of TNF-R.

In one embodiment, the present invention provides a composition comprising an isolated polynucleotide encoding a protein having TNF-R1-DD) ligand protein activity. In preferred embodiments, the polynucleotide is selected from the group consisting of:

(a) a polynucleotide comprising the nucleotide sequence of SEQ ID NO:1 from nucleotide 2 to nucleotide 1231;

(b) a polynucleotide comprising a fragment of the nucleotide sequence of SEQ ID NO:1;

(c) a polynucleotide encoding an TNF-R1-DD ligand protein comprising the amino acid sequence of SEQ ID NO:2;

(d) a polynucleotide encoding an TNF-R1-DD ligand protein comprising a fragment of the amino acid sequence of SEQ ID NO:2;

(e) a polynucleotide comprising the nucleotide sequence of SEQ ID NO:3 from nucleotide 2 to nucleotide 415;

(f) a polynucleotide comprising a fragment of the nucleotide sequence of SEQ ID NO:3;

(g) a polynucleotide encoding an TNF-R1-DD ligand protein comprising the amino acid sequence of SEQ ID NO:4;

(h) a polynucleotide encoding an TNF-R1-DD ligand protein comprising a fragment of the amino acid sequence of SEQ ID NO:4;

(i) a polynucleotide comprising the nucleotide sequence of SEQ ID NO:9 from nuclcotide 2 to nucleotide 931;

a polynucleotide comprising a fragment of the nucleotide sequence of SEQ ID NO:9;

(k) a polynucleotide encoding an TNF-R1-DD ligand protein comprising the amino acid sequence of SEQ ID NO:10;

(l) a polynucleotide encoding an TNF-R1-DD ligand protein comprising a fragment of the amino acid sequence of SEQ ID NO:10;

(m) a polynucleotide comprising the nucleotide sequence of SEQ ID NO:11 from nucleotide 2 to nucleotide 1822;

(n) a polynucleotide comprising a fragment of the nucleotide sequence of SEQ ID NO:11;

(o) a polynucleotide encoding an TNF-R1-DD) ligand protein comprising the amino acid sequence of SEQ ID NO:12;

(p) a polynucleotide encoding an TNF-R1-DD ligand protein comprising a fragment of the amino acid sequence of SEQ ID NO:12;

(q) a polynucleotide comprising the nucleotide sequence of SEQ ID NO:13 from nucleotide 3 to nucleotide 2846;

(r) a polynucleotide comprising a fragment of the nucleotide sequence of SEQ ID NO:13, which encodes a protein having TNF-R1-DD ligand protein activity;

(s) a polynucleotide encoding an TNF-R1-DD ligand protein comprising the amino acid sequence of SEQ ID NO:14;

(t) a polynucleotide encoding an TNF-R1-DD ligand protein comprising a fragment of the amino acid sequence of SEQ ID NO:14 and having TNF-R1-DD ligand protein activity; and (u) a polynucleotide capable of hybridizing under stringent conditions to any one of the polynucleotides specified in (a)–(t).

In certain preferred embodiments, the polynucleotide is operably linked to an expression control sequence. The invention also provides a host cell, including bacterial, yeast, insect and mammalian cells, transformed with such polynucleotide compositions.

Processes are also provided for producing an TNF-R1-DD ligand protein. which comprises:

(a) growing a culture of the host cell transformed with such polynucleotide compositions in a suitable culture medium; and (b) purifying the TNF-R1-DD ligand protein from the culture.

The ligand protein produced according to such methods is also provided by the present invention.

Compositions comprising a protein having TNF-R1-DD ligand protein activity are also disclosed. In preferred embodiments the protein comprises an amino acid sequence selected from the group consisting of:

(a) the amino acid sequence of SEQ ID NO:2;

(b) fragments of the amino acid sequence of SEQ ID NO:2;

(c) the amino acid sequence of SEQ ID NO:4;

(d) fragments of the amino acid sequence of SEQ ID NO:4;

(e) the amino acid sequence of SEQ ID NO:6;

(f) fragments of the amino acid sequence of SEQ ID NO:6;

(g) the amino acid sequence of SEQ ID NO:10;

(h) fragments of the amino acid sequence of SEQ ID NO:10;

(i) the amino acid sequence of SEQ ID NO:12;

(j) fragments of the amino acid sequence of SEQ ID NO:12;

(k) the amino acid sequence of SEQ ID NO:14; and (l) fragments of the amino acid sequence of SEQ ID NO:14;

the protein being substantially free from other mammalian proteins. Such compositions may further comprise a pharmaceutically acceptable carrier.

Compositions comprising an antibody which specifically reacts with such TNF-R1-DD ligand protein are also provided by the present invention.

Methods are also provided for identifying an inhibitor of TNF-R death domain binding which comprise:

(a) combining an TNF-R death domain protein with an TNF-R1-DD ligand protein, said combination forming a first binding mixture;

(b) measuring the amount of binding between the TNF-R death domain protein and the TNF-R1-DD ligand protein in the first binding mixture;

(c) combining a compound with the TNF-R death domain protein and an TNF-R1-DD ligand protein to form a second binding mixture;

(d) measuring the amount of binding in the second binding mixture; and (e) comparing the amount of binding in the first binding mixture with the amount of binding in the second binding mixture;

wherein the compound is capable of inhibiting TNF-R death domain binding when a decrease in the amount of binding of the second binding mixture occurs. In certain preferred embodiments the TNF-R1-DD ligand protein used in such method comprises an amino acid sequence selected from the group consisting of:

(a) the amino acid sequence of SEQ ID NO:2;

(b) fragments of the amino acid sequence of SEQ ID NO:2;

(c) the amino acid sequence of SEQ ID NO:4;

(d) fragments of the amino acid sequence of SEQ ID NO:4;

(e) the amino acid sequence of SEQ ID NO:6;

(f) fragments of the amino acid sequence of SEQ ID NO:6;

(g) the amino acid sequence of SEQ ID NO:8;

(h) fragments of the amino acid sequence of SEQ ID NO:8

(i) the amino acid sequence of SEQ ID NO:10;

(j) fragments of the amino acid sequence of SEQ ID NO:10;

(k) the amino acid sequence of SEQ ID NO:12;

(l) fragments of the amino acid sequence of SEQ ID NO:12;

(m) the amino acid sequence of SEQ ID NO:14; and (n) fragments of the amino acid sequence of SEQ ID NO:14.

Compositions comprising inhibitors identified according to such method are also provided. Such compositions may include pharmaceutically acceptable carriers.

Methods are also provided for preventing or ameliorating an inflammatory condition which comprises administering a therapeutically effective amount of a composition comprising a protein having TNF-R1-DD ligand protein activity and a pharmaceutically acceptable carrier.

Other embodiments provide methods of inhibiting TNF-R death domain binding comprising administering a therapeutically effective amount of a composition comprising a protein having TNF-R1-DD ligand protein activity and a pharmaceutically acceptable carrier.

Methods are also provided for preventing or ameliorating an inflammatory condition which comprises administering to a mammalian subject a therapeutically effective amount of a composition comprising a pharmaceutically acceptable carrier and a protein selected from the group consisting of insulin-like growth factor binding protein-5 ("IGFBP-5"), and fragments thereof having TNF-R1-DD ligand protein activity. Such proteins may also be administered for inhibiting TNF-R death domain binding.

Methods of preventing or ameliorating an inflammatory condition or of inhibiting TNF-R death domain binding are provided which comprise administering to a mammalian subject a therapeutically effective amount of inhibitors of TNF-R death domain binding, are also provided.

Methods of identifying an inhibitor of TNF-R death domain binding are also provided by the present invention which comprise:

(a) transforming a cell with a first polynucleotide encoding an TNF-R death domain protein, a second polynucleotide encoding an TNF-R1-DD ligand protein, and at least one reporter gene, wherein the expression of the reporter gene is regulated by the binding of the TNF-R1-DD ligand protein encoded by the second polynucleotide to the TNF-R death domain protein encoded by the first polynucleotide;

(b) growing the cell in the presence of and in the absence of a compound; and (c) comparing the degree of expression of the reporter gene in the presence of and in the absence of the compound;

wherein the compound is capable of inhibiting TNF-R death domain binding when a decrease in the degree of expression of the reporter gene occurs. In preferred embodiments, the cell is a yeast cell and the second polynucleotide is selected from the group consisting of:

(a) a polynucleotide comprising the nucleotide sequence of SEQ ID NO:1 from nucleotide 2 to nucleotide 1231;

(b) a polynucleotide comprising a fragment of the nucleotide sequence of SEQ ID NO:1, which encodes a protein having TNF-R1-DD ligand protein activity;

(c) a polynucleotide encoding an TNF-R1-DD ligand protein comprising the amino acid sequence of SEQ ID NO:2;

(d) a polynucleotide encoding an TNF-R1-DD ligand protein comprising a fragment of the amino acid sequence of SEQ ID NO:2 and having TNF-R1-DD ligand protein activity;

(e) a polynuclcotide comprising the nucleotide sequence of SEQ ID NO:3 from nucleotide 2 to nucleotide 415;

(i) a polynucleotide comprising a fragment of the nucleotide sequence of SEQ ID NO:3, which encodes a protein havinc, TNF-R1-DD ligand protein activity;

(g) a polynucleotide encoding an TNF-R1-DD ligand protein comprising the amino acid sequence of SEQ ID NO:4;

(h) a polynucleotide encoding an TNF-R1-DD ligand protein comprising a fragment of the amino acid sequence of SEQ ID NO:4 and having TNF-R1-DD ligand protein activity;

(i) a polynucleotide comprising the nucleotide sequence of SEQ ID NO:5 from nucleotide 2 to nucleotide 559;

(j) a polynucleotide comprising a fragment of the nucleotide sequence of SEQ ID NO:5, which encodes a protein having TNF-R1-DD ligand protein activity;

(k) a polynucleotide encoding an TNF-R1-DD ligand protein comprising the amino acid sequence of SEQ ID NO:6;

(l) a polynucleotide encoding an TNF-R1-DD ligand protein comprising a fragment of the amino acid sequence of SEQ ID NO:6 and having TNF-R1-DD ligand protein activity;

(m) a polynucleotide comprising the nucleotide sequence of SEQ ID NO:7 from nucleotide 57 to nucleotide 875;

(n) a polynucleotide comprising a fragment of the nucleotide sequence of SEQ ID NO:7, which encodes a protein having TNF-R1-DD ligand protein activity;

(o) a polynucleotide encoding an TNF-R1-DD ligand protein comprising the amino acid sequence of SEQ ID NO:8;

(p) a polynucleotide encoding an TNF-R1-DD ligand protein comprising a fragment of the amino acid sequence of SEQ ID NO:8 and having TNF-R1-DD ligand protein activity;

(q) a polynucleotide comprising the nucleotide sequence of SEQ ID NO:9 from nucleotide 2 to nucleotide 931;

(r) a polynucleotide comprising a fragment of the nucleotide sequence of SEQ ID NO:9;

(s) a polynucleotide encoding an TNF-R1-DD ligand protein comprising the amino acid sequence of SEQ ID NO:10;

(t) a polynucleotide encoding an TNF-R1-DD ligand protein comprising a fragment of the amino acid sequence of SEQ ID NO:10;

(u) a polynucleotide comprising the nucleotide sequence of SEQ ID NO:11 from nucleotide 2 to nucleotide 1822;

(v) a polynucleotide comprising a fragment of the nucleotide sequence of SEQ ID NO:11;

(w) a polynucleotide encoding an TNF-R1-DD ligand protein comprising the amino acid sequence of SEQ ID NO:12;

(x) a polynucleotide encoding an TNF-R1-DD ligand protein comprising a fragment of the amino acid sequence of SEQ ID NO:12;

(y) a polynucleotide comprising the nucleotide sequence of SEQ ID NO:13 from nucleotide 3 to nucleotide 2846;

(z) a polynucleotide comprising a fragment of the nucleotide sequence of SEQ ID NO:13, which encodes a protein having TNF-R1-DD ligand protein activity;

(aa) a polynucleotide encoding an TNF-R1-DD ligand protein comprising the amino acid sequence of SEQ ID NO:14;

(bb) a polynucleotide encoding an TNF-R1-DD ligand protein comprising a fragment of the amino acid sequence of SEQ ID NO:14 and having TNF-R1-DD ligand protein activity; and (cc) a polynucleotide capable of hybridizing under stringent conditions to any one of the polynucleotides specified in (a)–(bb), which encodes a protein having TNF-R1-DD ligand protein activity.

DETAILED DESCRIPTION OF THE INVENTION

Figure 1:
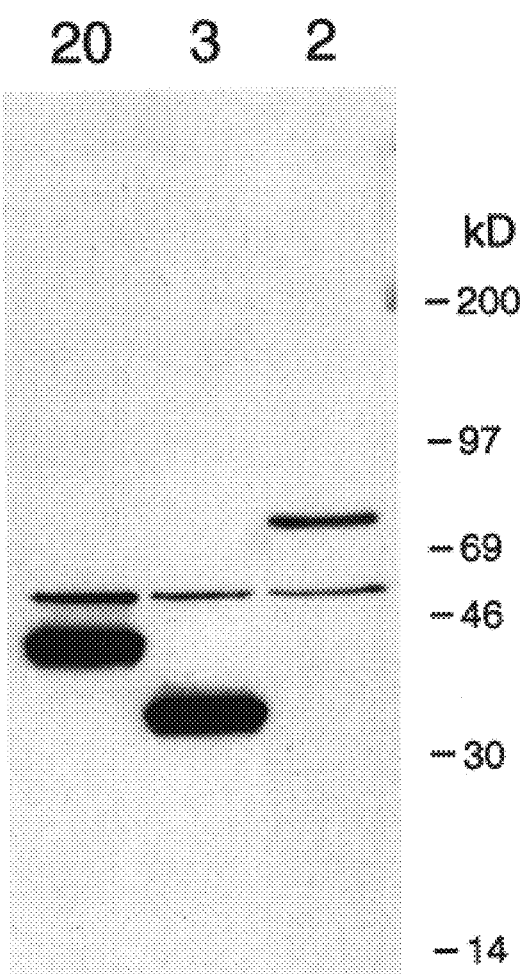
FIGS. 1 and 2 depict autoradiographs demonstrating the expression of TNF-R1-DD ligand proteins of the present invention.

The present inventors have for the first time identified and isolated novel polynucleotides which encode proteins which bind to the TNF-R death domain. As used herein "TNF-R" includes all receptors for tumor necrosis factor. The P55 type TNF-R is the preferred receptor for practicing the present invention.

The sequence of a polynucleotide encoding one such protein is set forth in SEQ ID NO:1 from nucleotides 2 to 1231. This polynucleotide has been identified as "clone 2DD" The amino acid sequence of the TNF-R1-DD ligand protein encoded by clone 2DD is set forth in SEQ ID NO:2. It is believed that clone 2DD is a partial cDNA clone of a longer full length coding sequence. However, as demonstrated herein the protein encoded by clone 2DD does bind the death domain of TNF-R (i.e., has "TNF-R1-DD ligand protein activity" as defined herein). Clone 2DD was deposited with the American Type Culture Collection on Oct. 13, 1994 and given the accession number ATCC 69706.

The protein encoded by clone 2DD is 410 amino acids in length. No identical or closely related sequences were found using BLASTN/BLASTX or FASTA searches. Therefore, clone 2DD encodes a novel protein.

The sequence of a polynucleotide encoding one such protein is set forth in SEQ ID NO:3 from nucleotides 2 to 415. This polynucleotide has been identified as "clone 3DD". The amino acid sequence of the TNF-R1-DD ligand protein encoded by clone 3DD is set forth in SEQ ID NO:4. It is believed that clone 3DD is a partial cDNA clone of a longer full length coding sequence. However, as demonstrated herein the protein encoded by clone 3DD does bind the death domain of TNF-R (i.e., has "TNF-R1-DD ligand protein activity" as defined herein). Clone 3DD was deposited with the American Type Culture Collection on Oct. 13, 1994 and given the accession number ATCC 69705.

The protein encoded by clone 3DD is 138 amino acids. No identical or closely related sequences were found using BLASTN/BLASTX or FASTA searches. Therefore, clone 3DD encodes a novel protein.

A full-length clone corresponding to clone 3DD was also isolated and identified as "clone 3TW". The nucleotide sequence of clone 3TW is reported as SEQ ID NO:13. Nucleotides 3 to 2846 of SEQ ID NO:13 encode a TNF-R1-DD ligand protein, the amino acid sequence of which is reported as SEQ ID NO:14. Amino acids 811 to 948 of SEQ ID NO:14 correspond to amino acids 1 to 138 of SEQ ID NO:4 (clone 3DD). Clone 3TW was deposited with the American Type Culture Collection on Sep. 26, 1995 and given the accession number ATCC 69904.

The sequence of a polynucleotide encoding another such protein is set forth in SEQ ID NO:5 from nucleotides 2 to 559. This polynucleotide has been identified as "clone 20DD." The amino acid sequence of the TNF-R1-DD ligand protein encoded by clone 20DD is set forth in SEQ ID NO:6. It is believed that clone 20DD is a partial cDNA clone of a longer full length coding sequence. However, as demonstrated herein the protein encoded by clone 20DD does bind the death domain of TNF-R (i.e., has "TNF-R1-DD ligand protein activity" as defined herein). Clone 20DD was deposited with the American Type Culture Collection on Oct. 13, 1994 and given the accession number ATCC 69704.

The protein encoded by clone 20DD is identical to amino acids 87 to 272 of insulin-like growth factor binding protein-5 ("IGFBP-5"), a sequence for which was disclosed in J. Biol. Chem. 266:10646–10653 (1991) by Shimasaki et al., which is incorporated herein by reference. The polynucleotide and amino acid sequences of IGFBP-5 are set forth in SEQ ID NO:7 and SEQ ID NO:8, respectively. Based upon the sequence identity between clone 20DD and IGFBP-5, IGFBP-5 and certain fragments thereof will exhibit TNF-R1-DD ligand binding activity (as defined herein).

The sequence of a polynucleotide encoding another such protein is set forth in SEQ ID NO:9 from nucleotides 2 to 931. This polynucleotide has been identified as "clone 1TU". The amino acid sequence of the TNF-R1-DD ligand protein encoded by clone 1TU is set forth in SEQ ID NO:10. It is believed that clone 1TU is a partial cDNA clone of a longer full length coding sequence. However, as demonstrated herein the protein encoded by clone 1TU does bind the death domain of TNF-R (i.e., has "TNF-R1-DD ligand protein activity" as defined herein). Clone 1TU was deposited with the American Type Culture Collection on Jun. 7, 1995 and given the accession number ATCC 69848.

The protein encoded by clone 1TU is 310 amino acids in length. No identical or closely related sequences were found using BLASTN/BLASTX or FASTA searches. Therefore, clone 1TU encodes a novel protein.

The sequence of a polynucleotide encoding another such protein is set forth in SEQ ID NO:11 from nucleotides 2 to 1822. This polynucleotide has been identified as "clone 27TU". The amino acid sequence of the TNF-R1-DD ligand protein encoded by clone 27TU is set forth in SEQ ID NO:12. It is believed that clone 27TU is a partial cDNA clone of a longer full length coding sequence. However, as demonstrated herein the protein encoded by clone 27TU does bind the death domain of TNF-R (i.e., has "TNF-R1-DD ligand protein activity" as defined herein). Clone 27TU was deposited with the American Type Culture Collection on Jun. 7, 1995 and given the accession number ATCC 69846.

Thre protein encoded by clone 27TU is 607 amino acids in length. No identical or closely related sequences were found using BLASTN/BLASTX or FASTA searches. Therefore, clone 27TU encodes a novel protein. 27TU may be a longer version of clone 2DD. 2DD encodes the same amino acid sequence (SEQ ID NO:2) as amino acids 198–607 encoded by 27TU (SEQ ID NO:12). The nucleotide sequences of 2DD and 27TU are also identical within this region of identity.

An additional "clone 15TU" was isolated which encoded a portion of the 27TU sequence (approximately amino acids 289–607 of SEQ ID NO:12). Clone 15TU was deposited with the American Type Culture Collection on Jun. 7, 1995 and given the accession number ATCC 69847. 15TU comprises the same nucleotide sequence as 27TU over this region of amino acids.

Polynucleotides hybridizing to the polynucleotides of the present invention under stringent conditions and highly stringent conditions are also part of the present invention. As used herein, "highly stringent conditions" include, for example, 0.2×SSC at 65° C.; and "stringent conditions" include, for example, 4×SSC at 65° C. or 50% formamide and 4×SSC at 42° C.

For the purposes of the present application, "TNF-R1-DD ligand protein" includes proteins which exhibit TNF-R1-DD ligand protein activity. For the purposes of the present application, a protein is defined as having "TNF-R1-DD ligand protein activity" when it binds to a protein derived from the TNF-R death domain. Activity can be measured by using any assay which will detect binding to an TNF-R death domain protein. Examples of such assays include without limitation the interaction trap assays and assays in which TNF-R death domain protein which is affixed to a surface in a manner conducive to observing binding, including without limitation those described in Examples 1 and 3. As used herein an "TNF-R death domain protein" includes the entire death domain or fragments thereof.

Fragments of the TNF-R1-DD ligand protein which are capable of interacting with the TNF-R death domain or which are capable of inhibiting TNF-R death domain binding (i.e., exhibit TNF-R1-D)D ligand protein activity) are also encompassed by the present invention. Fragments of the TNF-R1-DD ligand protein may be in linear form or they may be cyclized using known methods, for example, as described in H. U. Saragovi et al., Bio/Technology 10, 773–778 (1992) and in R. S. McDowell, et al.; J. Amer. Chem. Soc. 114, 9245–9253 (1992), both of which are incorporated herein by reference. Such fragments may be fused to carrier molecules such as immunoglobulins for many purposes, including increasing the valency of TNF-R1-DD ligand protein binding sites. For example, fragments of the TNF-R1-DD ligand protein may be fused through "linker" sequences to the Fc portion of an immunoglobulin. For a bivalent form of the TNF-R1-DD ligand protein, such a fusion could be to the Fc portion of an IgG molecule. Other immunoglobulin isotypes may also be used to generate such fusions. For example, an TNF-R1-DD ligand protein—IgM fusion would generate a decavalent form of the TNF-R1-DD ligand protein of the invention.

The isolated polynucleotide of the invention may be operably linked to an expression control sequence such as the pMT2 or pED expression vectors disclosed in Kaufman et aL, Nucleic Acids Res. 19, 4485–4490 (1991), in order to produce the TNF-R1-DD ligand protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and the expression control sequence are situated within a vector or cell in such a way that the TNF-R 1-DD ligand protein is expressed by a host cell which has been transformed (transfected) with the ligated polynucleotide/expression control sequence.

A number of types of cells may act as suitable host cells for expression of the TNF-R1-DD ligand protein. host cells include, for example, monkey COS cells, Chinese Hamster Ovary (CHO) cells, human kidney 293 cells, human epidermal A431 cells, human Colo205 cells, 3T3 cells, CV-1 cells. other transformed primate cell lines, normal diploid cells, cell strains derived from in vitro culture of primary tissue, primary explants, HeLa cells, mouse L cells, BHK, HL-60, U937, HaK or Jurkat cells.

The TNF-R1-DD ligand protein may also be produced by operably linking the isolated polynucleotide of the invention to suitable control sequences in one or more insect expression vectors, and employing an insect expression system. Materials and methods for baculovirus/inisect cell expression systems are commercially available in kit form from, e.g., Invitrogen, San Diego, Calif. U.S.A. (the MaxBac® kit). and such methods are well known in the art, as described in Summers and Smith, *Texas Agricultural Experiment Station Bulletin No.* 1555 (1987), incorporated herein by reference.

Alternatively, it may be possible to produce the TNF-R1-DD ligand protein in lower eukaryotes such as yeast or in prokaryotes such as bacteria. Potentially suitable yeast strains include *Saccharomyces cerevisiae, Schizosaccharomyces pombe*, Kluyveromyces strains, Candida, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the TNF-R1-DD ligand protein is made in yeast or bacteria, it may be necessary to modify the protein produced therein, for example by phosphorylation or glycosylation of the appropriate sites, in order to obtain the functional TNF-R1-DD ligand protein. Such covalent attachments may be accomplished using known chemical or enzymatic methods.

The TNF-R1-DD ligand protein of the invention may also be expressed as a product of transgenic animals, e.g., as a component of the milk of transgenic cows, goats, pigs, or sheep which are characterized by somatic or germ cells containing a nucleotide sequence encoding the TNF-R1-DD ligand protein.

The TNF-R1-DD ligand protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the TNF-R1-DD ligand protein may also include an affinity column containing the TNF-R death domain or other TNF-R death domain protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the TNF-R1-DD ligand protein of the invention may also be expressed in a form which will facilitate purification. For example, it may be expressed as a fusion protein, such as those of maltose binding protein (MBP) or glutathione-S-transferase (GST). Kits for expression and purification of such fusion proteins are commercially available from New England BioLab (Beverly, Mass.) and Pharmacia (Piscataway, N.J.), respectively. The TNF-R ligand protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the TNF-R1-DD ligand protein. Some or all of the foregoing purification steps, in various combinations, can also be employed to provide a substantially homogeneous isolated recombinant protein. The TNF-R1-DD ligand protein thus purified is substantially free of other mammalian proteins and is defined in accordance with the present invention as an "isolated TNF-R1-DD ligand protein."

TNF-R1-DD ligand proteins may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with TNF-R1-DD ligand proteins may possess biological properties in common therewith, including TNF-R1-DD ligand protein activity. Thus, they may be employed as biologically active or immunological substitutes for natural, purified TNF-R1-DD ligand proteins in screening of therapeutic compounds and in immunological processes for the development of antibodies.

The TNF-R1-DD ligand proteins provided herein also include proteins characterized by amino acid sequences similar to those of purified TNF-R1-DD ligand proteins but into which modification are naturally provided or deliberately engineered. For example, modifications in the peptide or DNA sequences can be made by those skilled in the art using known techniques. Modifications of interest in the TNF-R1-DD ligand protein sequences may include the replacement, insertion or deletion of a selected amino acid residue in the coding sequence. For example, one or more of the cysteine residues niav be deleted or replaced wvith another amino acid to alter the coniormiiationi of the molecule. Mutaltagenic techniques for such replacement, insertion or deletion are well known to those skilled in the art (see, e.g., U.S. Pat. No. 4,518,584).

Other fragments and derivatives of the sequences of TNF-R1-DD ligand proteins which would be expected to retain TNF-R1-DD ligand protein activity in whole or in part and may thus be useful for screening or other immunological methodologies may also be easily made by those skilled in the art given the disclosures herein. Such modifications are believed to be encompassed by the present invention.

TNF-R1-DD ligand protein of the invention may also be used to screen for agents which are capable of inhibiting or blocking binding of an TNF-R1-DD ligand protein to the death domain of TNF-R, and thus may act as inhibitors of TNF-R death domain binding and/or TNF activity. Binding assays using a desired binding protein, immobilized or not, are well known in the art and may be used for this purpose using the TNF-R1-DD ligand protein of the invention. Examples 1 and 3 describe examples of such assays. Appropriate screening assays may be cell-based or cell-free. Alternatively, purified protein based screening assays may be used to identify such agents. For example, TNF-R1-DD ligand protein may be immobilized in purified form on a carrier and binding to purified TNF-R death domain may be measured in the presence and in the absence of potential inhibiting agents. A suitable binding assay may alternatively employ purified TNF-R death domain immobilized on a carrier, with a soluble form of a TNF-R1-DD ligand protein of the invention. Any TNF-R1-DD ligand protein may be used in the screening assays described above.

In such a screening assay, a first binding mixture is formed by combining TNF-R death domain protein and TNF-R1-DD ligand protein, and the amount of binding in the first binding mixture ($B_o$) is measured. A second binding mixture is also formed by combining TNF-R death domain protein, TNF-R1-DD ligand protein, and the compound or agent to be screened, and the amount of binding in the second binding mixture (B) is measured. The amounts of binding in the first and second binding mixtures are compared, for example, by performing a $B/B_o$ calculation. A compound or agent is considered to be capable of inhibiting TNF-R death domain binding it a decrease in binding in the second binding mixture as compared to the first binding mixture is observed. The formulation and optimization of binding mixtures is within the level of skill in the art. Such binding mixtures may also contain buffers and salts necessary to enhance or to optimize binding, and additional control assays may be included in the screening assay of the invention.

Alternatively, appropriate screening assays may be cell based. For example, the binding or interaction between an TNF-R ligand protein and the TNF-R death domain can be measured in yeast as described below in Examples 1 and 3.

Compounds found to reduce, preferably by at least about 10%, more preferably greater than about 50% or more, the binding activity of TNF-R1-DD ligand protein to TNF-R death domain may thus be identified and then secondarily screened in other binding assays, including in vivo assays. By these means compounds having inhibitory activity for TNF-R death domain binding which may be suitable as anti-inflammatory agents may be identified.

Isolated TNF-R1-DD ligand protein may be useful in treating, preventing or ameliorating inflammatory conditions and other conditions, such as cachexia, autoimmune disease, graft versus host reaction, osteoporosis, colitis, myelogenous leukemia, diabetes, wasting, and atherosclerosis. Isolated TNF-R1-DD ligand protein may be used itself as an inhibitor of TNF-R death domain binding or to design inhibitors of TNF-R death domain binding. Inhibitors of binding of TNF-R1-DD ligand protein to the TNF-R death domain ("TNF-R intracellular binding inhibitors") are also useful for treating such conditions.

The present invention encompasses both pharmaceutical compositions and therapeutic methods of treatment or use which employ isolated TNF-R1-DD ligand protein and/or binding inhibitors of TNF-R intracellular binding.

Isolated TNI-R1-DD ligand protein or binding inhibitors (from whatever source derived, including without limitation from recombinant and non-recombinant cell lines) may be used in a pharmaceutical composition when combined with a pharmaceutically acceptable carrier. Such a composition may also contain (in addition to TNF-R1-DD ligand protein or binding inhibitor and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-2, IL-3, IL-4, IL-5, IL-6, IL-7, IL-8, IL-9, G-CSF, Meg-CSF, stem cell factor, and erythropoietin. The pharmaceutical composition may further contain other anti-inflammatory agents. Such additional factors and/or agents may be included in the pharmaceutical composition to produce a synergistic effect with isolated TNF-R1-DD ligand protein or binding inhibitor, or to minimize side effects caused by the isolated TNF-R1-DD ligand protein or binding inhibitor. Conversely, isolated TNF-R1-DD ligand protein or binding inhibitor may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammmatory agent.

The pharmaceutical composition of the invention may be in the form of a liposome in which isolated TNF-R1-DD ligand protein or binding inhibitor is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of an inflammatory response or condition, or an increase in rate of treatment, healing, prevention or amelioration of such conditions. When applied to an individual active in(iredieit, administered alone, the term refers to that ingredient alone. When applied to a combination the term refers to combined amounts of the active ingredients that result in the therapeutic effect, whether administered in combination, serially or simultaneously.

In practicing the method of treatment or use of the present invention, a therapeutically effective amount of isolated TNF-R1-DD ligand protein or binding inhibitor is administered to a mammal having a condition to be treated. Isolated TNF-R1-DD ligand protein or binding inhibitor may be administered in accordance with the method of the invention either alone or in combination with other therapies such as treatments employing cytokines, lymphokines or other hematopoietic factors. When co-administered with one or more cytokines, lymphokines or other hematopoietic factors, isolated TNF-R1-DD ligand protein or binding inhibitor may be administered either simultaneously with the cytokine(s), lymphokine(s), other hematopoictic factor(s), thrombolytic or anti-thrombotic factors, or sequentially. If administered sequentially, the attending physician will decide on the appropriate sequence of administering isolated TNF-R1-DD ligand protein or binding inhibitor in combination with cytokine(s), lymphokine(s), other hematopoietic factor(s), thrombolytic or anti-thrombotic factors.

Administration of isolated TNF-R1-DD ligand protein or binding inhibitor used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of isolated TNF-R1-DD ligand protein or binding inhibitor is administered orally, isolated TNF-R1-DD ligand protein or binding inhibitor will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% isolated TNF-R1-DD ligand protein or binding inhibitor, and preferably from about 25 to 90% isolated TNF-R1-DD ligand protein or binding inhibitor. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of isolated TNF-R1-DD ligand protein or binding inhibitor, and preferably from about 1 to 50% isolated TNF-R1-DD ligand protein or binding inhibitor.

When a therapeutically effective amount of isolated TNF-R1-DD ligand protein or binding inhibitor is administered by intravenous, cutaneous or subcutaneous injection, isolated TNF-R1-DD ligand protein or binding inhibitor will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to isolated TNF-R1-DD ligand protein or binding inhibitor, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of isolated TNF-R1-DD ligand protein or binding inhibitor in the pharmaceutical composition of the present invention will depend upon the nature and severity of the condition being treated, and on the nature of prior treatments which the patient has undergone. Ultimately, the attending physician will decide the amount of isolated TNF-R1-DD ligand protein or binding inhibitor with which to treat each individual patient. Initially, the attending physician will administer low doses of isolated TNF-R1-DD ligand protein or binding inhibitor and observe the patient's response. Larger doses of isolated TNF-R1-DD ligand protein or binding inhibitor may be administered until the optimal therapeutic effect is obtained for the patient, and at that point the dosage is not increased further. It is contemplated that the various pharmaceutical compositions used to practice the method of the present invention should contain about 0.1 $\mu$g to about 100 mg of isolated TNF-R1-DD ligand protein or binding inhibitor per kg body weight.

The duration of intravenous therapy using the pharmaceutical composition of the present invention will vary, depending on the severity of the disease being treated and the condition and potential idiosyncratic response of each individual patient. It is contemplated that the duration of each application of the isolated TNF-R1-DD ligand protein or binding inhibitor will be in the range of 12 to 24 hours of continuous intravenous administration. Ultimately the attending physician will decide on the appropriate duration of intravenous therapy using the pharmaceutical composition of the present invention.

Isolated TNF-R1-DD ligand protein of the invention may also be used to immunize animals to obtain polyclonal and monoclonal antibodies which specifically react with the TNF-R1-DD ligand protein and which may inhibit TNF-R death domain binding. Such antibodies may be obtained using either the entire TNF-R1-DD ligand protein or fragments of TNF-R1-DD ligand protein as an imnmunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer.Chem.Soc. 85, 2149–2154 (1963); J. L. Krstenansky, et al., FEBS Lett. 211, 10 (1987).

Monoclonal antibodies binding to TNF-R1-DD ligand protein or to complex carbohydrate moieties characteristic of the TNF-R1-DD ligand glycoprotein may be useful diagnostic agents for the immunodetection of TNF-R ligand protein.

Neutralizing monoclonal antibodies binding to TNF-R1-DD ligand protein or to complex carbohydrates characteristic of TNF-R1-DD ligand glycoprotein may also be useful therapeutics for both inflammatory conditions and also in the treatment of some forms of cancer where abnormal expression of TNF-R1-DD ligand protein is involved. These neutralizing monoclonal antibodies are capable of blocking the signaling function of the TNF-R1-DD ligand protein. By blocking the binding of TNF-R1-DD ligand protein, certain biological responses to TNF are either abolished or markedly reduced. In the case of cancerous cells or leukemic cells, neutralizing monoclonal antibodies against TNF-R1-DD ligand protein may be useful in detecting and preventing the metastatic spread of the cancerous cells, which may be mediated by the TNF-R1-DD ligand protein.

Due to the similarity of their sequences to the insulin growth factor binding protein ("IGFBP-5") and fragments thereof which bind to the TNF-R death domain are proteins having TNF-R1-DD ligand protein activity as defined herein. As a result, they are also usefuil in pharmaceutical compositions, for treating inflammatory conditions and for inhibiting TNF-R death domain binding as described above for TNF-R1-DD ligand proteins generally.

EXAMPLE 1

CLONING OF TNF-R DEATH DOMAIN LIGAND PROTEIN ENCODING POLYNUCLEOTIDE

A yeast genetic selection method, the "interaction trap" [Gyuris et al, Cell 75:791–803, 1993, which is incorporated herein by reference], was used to screen WI38 cell cDNA libraries (preparation, see below) for proteins that interact with the death domain of the P55 type 1 TNF receptor (TNF-R1-DD). A polynucleotide encoding amino acids 326 to 413 of the P55 type TNF receptor, TNF-R1-DD, was obtained via the polymerase chain reaction (PCR) using a grafting method. This TNF-R1-DD DNA was then cloned into pEG202 by BamHI and SalI sites, generating the bait plasmid, pEG202-TNF-R1-DD. This plasmid contains the HIS3 selectable marker, and expression of the bait, the LexA-TNF-R1-DD fusion protein, is from the strong constitutive ADH1 promoter. To create the reporter strain carrying the bait protein, yeast strain EGY48, containing the reporter sequence LexAop-Leu2 in place of the chromosomal LEU2, was transformed with pEG202-TNF-R1-DD and pSH18–34 (Ura+), which carries another reporter sequence. LexAop-lacZ. For screening cDNAs encoding proteins that interact with TNF-R1-DD, the expression vector pJG4–5 (TRP1, containing the WI38 cell cDNA library (see below for the cDNA library construction), was transformed into the above strain (EGY48/pEG202-TNF-R1-DD/pSH18–34) according to the method described by Gietz et al., Nucleic Acids Res., 20:1425 (1992).

cDNA Library Construction:

WI38 cell cDNA library: Double stranded cDNA was prepared from 3 ug of WI38 mRNA using reagents provided by the Superscript Choice System (Gibco/BRL, Gaithersberg, Md.) with the following substitutions: the first strand synthesis was primed using an oligo dT/XhoI primer/linker, and the dNTP mix was substituted with a mix containing methyl dCTP (Stratagene, LaJolla, Calif.). The cDNA was modified at both ends by addition of an EcoRI/NotI/SalI adapter linker and subsequently digested with XhoI. This produced cDNA molecules possessing an EcoRI/NotI/SalI overhang at the 5' end of the gene and an XhoI overhang at the 3' end. These fragments were then ligated into the yeast expression/fusion vector pJG4–5 (Gyuris et al., Cell, 75, 791–803, 1993), which contains at its amino terminus, the influenza virus HA1 epitope tag, the B42 acidic transcription activation domain, and the SV40 nuclear localization signal, all under the control of the galactose-dependentGAL 1 promoter. The resulting plasmids were then electroporated into DH10B cells (Gibco/BRL). A total of $7.1\times10^6$ colonies were plated on LB plates containing 100 ug/ml of ampicillin. These *E.coli* were scraped, pooled, and a large scale plasmid prep was performed using the Wizard Maxi Prep kit (Promega, Madison, Wis.), yielding 3.2 mg of supercoiled plasmid DNA.

WI38 Cell cDNA Screening Results:

$1\times10^6$ transformants were obtained on glucose $Ura^-His^-Trp^-$ plates. These transformants were pooled and resuspended in a solution of 65% glycerol, 10 mM Tris-HCl (pH 7.5), 10 mM $MgCl_2$ and stored at −80° C. in 1 mL aliquots. For screening purposes, aliquots of these were diluted 10-fold into $Ura^-His^-Trp^-$ CM dropout gal/raff medium (containing 2% galactose, 1% raffinose), which induces the expresssion of the library encoded proteins, and incubated at 30° C. for 4 hours. $12\times10^6$ colony forming units (CFUs) were then plated on standard 10 cm galactose X-Gal $Ura^-His^-Trp^-Leu^-$ plates at a density of $2\times10^5$ CFU/plate. After three days at 30° C., about 1,000 colonies were formed ($Leu^+$) and of those, sixty-four colonies were $LacZ^+$. In order to test if the $Leu^+/LacZ^+$ phenotype was due to the library-encoded protein, the galactose dependency of the phenotype was tested. Expression of the library-encoded proteins was turned off by growth on glucose $Ura^-His^-Trp^-$ master plates and then retested for galactose-dependency on glucose $Ura^-His^-Trp^-Leu^+$, galactose $Ura^-His^-Trp^-Leu^+$, glucose X-Gal $Ura^-His^-Trp^-$, and galactose X-Gal $Ura^-His^-Trp^-$ plates. Of these, 32 colonies showed galactose-dependent growth on $Leu^-$ plates and galactose-dependent blue color on X-Gal-containing medium ($LacZ^+$ phenotype). Total yeast DNA was prepared from these colonies according to the method described previously (Hoffman and Winston, 1987). In order to analyze the cDNA sequences, PCR reactions were performed using the above yeast-DNA as a template and oligo primers specific for the vector pJG4–5, flanking the cDNA insertion point. PCR products were purified (Qiagen PCR purification kit), subjected to restriction digest with the enzyme HaeIII, run on 1.8% agarose gels, and the restriction patterns compared. Similar and identical restriction patterns were grouped and representatives of each group were sequenced and compared to Genbank and other databases to identify any sequence homologies.

One clone of unique sequence ("2DD") and three clones with identical sequence ("3DD") were isolated and showed no signficant sequence homologies compared to Genbank and other databases. Additionally, four other clones ("20DD") with identical sequence to a portion of human insulin-like growth factor binding protein-5 (Shunichi Shimasaki et al., J. Biol. Chem. 266:10646–10653 (1991)) were isolated. The clones "2DD," "3DD" and "20DD" were chosen for further analysis. Library vector pJG4–5 containing these clones sequences were rescued from yeast by transforming the total yeast DNAs into the *E. coli* strain KC8 and selecting for growth on Trp-ampicillin plates. These putative TNFR1 interacting proteins were then tested further for specificity of interaction with the TNF-R1-DD by the reintroduction of JG4–5 clone into EGY48 derivatives containing a panel of different baits, including bicoid, the cytoplasmic domain of the IL-1 receptor, and TNF-R1-DD. The above clones were found to interact only with the TNF-R1-DD. The interaction between these clones and TNF-R1-DD was thus judged to be specific.

U937 cDNA Screening Results:

A U937 cDNA library was also constructed and screened as described above. 1,020 Leu+ colonies were found and of those, 326 colonies were also LacZ+. 62 colonies of these Leu+/LacZ+ colonies showed a galactose-dependent phenotype. One of these clones, 1TU, encodes a novel sequence. Interestingly, two clones. 15TU and 27TU, encode related or identical sequences. except that 27TU contains about 864 additional nucleotides (or about 288 amino acids) at the 5' end. 15/27TU also encode a novel sequence.

EXAMPLE 2

EXPRESSION OF THE TNF-R1-DD Ligand PROTEIN cDNAs encoding TNF-R intracellular ligand proteins were released from the pJG4–5 vector with the appropriate restriction enzymes. For example, EcoRI and XhoI or NotI and XhoI were used to release cDNA from clone 2DD and clone 20DD. Where the restriction sites were also present in the internal sequence of the cDNA, PCR was performed to obtain the cDNA. For example, the cDNA fragment encoding "clone 3DD" was obtained through PCR due to the presence of an internal XhoI site. These cDNAs were then cloned into various expression vectors. These included pGEX (Pharmacia) or pMAL (New England Biolabs) for expression as a GST (Glutathione-S-transferase) or MBP (maltose binding protein) fusion protein in E. coli, a pED-based vector for mammalian expression, and pVL or pBlueBacHis (Invitrogen) for baculovirus/insect expression. For the immunodetection of TNF-R intracellular ligand expression in manmnalian cells, an epitope sequence, "Flag," was inserted into the translational start site of the pED vector, generating the pED-Flag vector. cDNAs were then inserted into the pED-Flag vector. Thus, the expression of cDNA from pED-Flag yields a protein with an amino terminal Met, followed by the "Flag" sequence, Asp-Tyr-Lys-Asp-Asp-Asp-Asp-Lys (SEQ ID No:15). Standard DEAE-Dextran or lipofectamine methods were used to transfect COS or CHO dukx cells. Immunodetection of Flag-tagged proteins was achieved using the M2 antibody (Kodak). Moreover, an immunoaffinity column using the M2 antibody, followed by elution with the "Flag" peptide, can be used for the rapid purification of the flag-tagged protein. Similarly, affinity purification of GST-, MBP- or His-tagged fusion proteins can be performed using glutathione, amylose, or nickel columns. Detailed purification protocols are provided by the manufacturers. For many fusion proteins, the TNF-R intracellular ligand can be released by the action of thrombin, factor Xa, or enterokinase cleavage. In the case where highly purified material is required, standard purification procedures, such as ion-exchange, hydrophobic, and gel filtration chromatography will be applied in addition to the affinity purification step.

Figure 2:
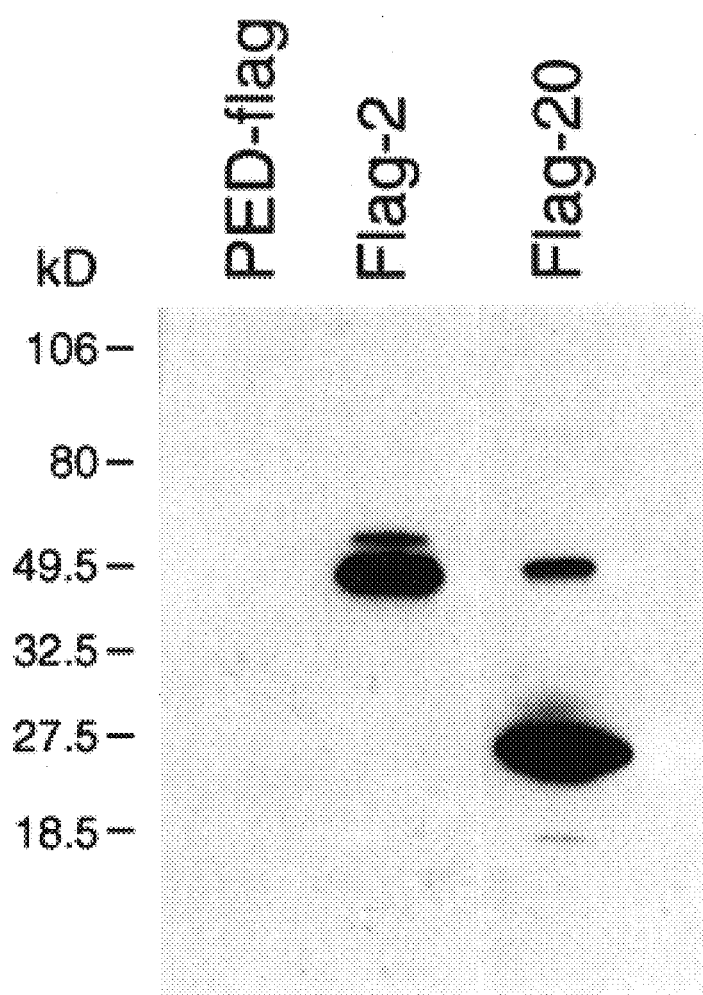

FIGS. 1 and 2 depict autoradiographs demonstrating the expression of TNF-R1-DD ligand proteins in yeast and mammalian cells. FIG. 1 shows the results of expression of isloated clones of the present invention in yeast. EGY48 was transformed with pJG4–5 containing clone 2DD, 3DD or 20DD. Cells were then grown overnight in the galactose/raffinose medium. Cell lysates were prepared and subject to 4–20% SDS gel electrophoresis, followed by Western blot analysis using anti-HA antibody (12CA5, Boehringer Mannheim, Indianapolis, Ind.). FIG. 2 shows the results of expression of Flag-2DD and Flag-20DD in COS cells. COS cells were transfected with either pED-Flag (Vector control), Flag-2DD or Flag-20DD plasmid by the lipofectamine method. Thirty µg of each cell lysate were prepared and subjected to 4–20% SDS gel electrophoresis, followed by Western blot analysis using M2 antibody (Kodak). The bands in the Flag-2DD and Flag-20DD lanes indicate significant expression of the respective TNF-R1-DD ligand proteins.

EXAMPLE 3

ASSAYS OF TNF-R DEATH DOMAIN BINDING

Two different methods were used to assay for TNF-R1-DD ligand protein activity. The first assay measures binding in the yeast strain in "interaction trap," the system used here to screen for TNF-R1-DD interacting proteins. In this system, the expression of reporter genes from both LexAop-Leu2 and LexAop-LacZ relies on the interaction between the bait protein, in this case TNF-R1-DD, and the prey, the TNF-R intracellular ligand. Thus, one can measure the strength of the interaction by the level of Leu2 or LacZ expression. The most simple method is to measure the activity of the LacZ encoded protein, β-galactosidase. This activity can be judged by the degree of blueness on the X-Gal containing medium or filter. For the quantitative measurement of β-galactosidase activity. standard assays can be found in "Methods in Yeast Genetics" Cold Spring Harbor, N.Y., 1990 (by Rose, M. D., Winston, F., and Hieter, P.).

The second assay tor measuring binding is a cell-free system. An example of a typical assay is described below. Purified GST-TNF-R1-DD fusion protein (2 ug) was mixed with amylose resins bound with a GST-TNF-R1-DD intracellular ligand for 2 hour at 4° C. The mixture was then centrifuiged to separate bound (remained with the beads) and unbound (remained in the supernatant) GST-TNF-R1-DD. After extensive washing, the bound GST-TNF-R1-DD- was eluted with maltose and detected by Western blot analysis using a GST antibody. The TNF-R1-DD or the intracellular ligand can also be immobilized on other solid supports, such as on plates or fluorobeads. The binding can then be measured using ELISA or SPA (scintillation proximity assay).

EXAMPLE 4

CHARACTERIZATION OF TNF-R DEATH DOMAIN LIGAND PROTEIN

Mapping the Interaction Site in TNF-R1

Many of the key amino acids for TNF-R signaling have been determined by site-directed mutagenesis (Tataglia et al., Cell 74:845–853 (1993). These amino acids are conserved between TNF-R and the Fas antigen, which is required for mediating cytotoxicity and other cellular responses. In order to test if the TNF-R intracellular proteins interact with these residues, the following mutations were constructed: F345A (substitution of phe at amino acid 345 to Ala), R347A, L351A, F345A/R347A/L351A, E369A, W378A and I408A. The ability of the mutant protein to interact with the intracellular ligand in the "interaction trap" system was tested.

Effect on the TNF-Mediated Response

The effect of the TNF-R intracellular ligands on the TNF-mediated response can be evaluated in cells overexpressing the ligands. A number of TNF-mediated responses, including transient or prolonged responses, can be measured. For example, TNF-induced kinase activity toward either MBP (myelin basic protein) or the N-terminus (amino acids 1–79) of c-jun can be measured in COS cells or CHO cells either transiently or stably overexpressing clone 2DD, 3DD or clone 20DD. The significance of these ligand proteins in TNF-mediated cytotoxicity and other cellular responses can be measured in L929 or U937 overexpressing cells. Alternatively, other functional assays, such as the induction of gene expression or $PGE_2$ production after prolonged incubation with TNF, can also be used to measure the TNF mediated response. Conversely, the significance of the TNF-R1-DD ligand proteins in TNF signaling can be established by lowering or eliminating the expression of the ligands. These experiments can be performed using antisense expression or transgenic mice.

Enzymatic or Functional Assays

The signal transduction events initiated by TNF binding to its receptor are still largely unknown. However, one major result of TNF binding is the stimulation of cellular serine/threonine kinase activity. In addition, TNF has been shown to stimulate the activity of PC-PLC, $PLA_2$, and sphingomyelinase. Therefore, some of the TNF-R1-DD ligand proteins may possess intrinsic enzymatic activity that is responsible for these activities. Therefore, enzymatic assays can be performed to test this possibility, particularly with those clones that encode proteins with sequence homology to known enzymes. In addition to enzymatic activity, based on the sequence homology to proteins with known function, other functional assays can also be measured.

EXAMPLE 5

ISOLATION OF FULL LENGTH CLONES

In many cases, cDNAs obtained from the interaction trap method each encode only a portion of the full length protein. For example, based on identity and sequence and the lack of the initiating methionine codon, clones 2DD, 3DD and 20DD apparently do not encode full length proteins. Therefore, it is desirable to isolate full length clones. The cDNAs obtained from the screening, such as clone 2DD, are used as probes, and the cDNA libraries described herein, or alternatively phage cDNA libraries, are screened to obtain full length clones in accordance with known methods (see for example, "Molecular Cloning, A laboratory Manual", by Sambrook et al., 1989 Cold Spring Harbor).

EXAMPLE 6

ANTIBODIES SPECIFIC FOR TNF-R INTRACELLULAR LIGAND PROTEIN

Antibodies specific for TNF-R intracellular ligand proteins can be produced using purified recombinant protein, as described in Example 2, as antigen. Both polyclonal and monoclonal antibodies will be produced using standard techniques, such as those described in "Antibodies, a Laboratory Manual" by Ed Harlow and David Lane (1988), Cold Spring Harbor Laboratory.

EXAMPLE 7

CHARACTERIZATION OF CLONES 1TU AND 15/27TU

Specificity of Interaction

The specificity of clones 1TU, 15TU and 27TU was tested using a panel of baits. The ability of these clones to bind the TNF-R death domain was compared to their binding to the intracellular domain of the second TNF-R (TNF-R $p75_{IC}$), the entire intracellular domain of TNF-R (TNF-R $p55_{IC}$), the death domain of the fas antigen (which shares 28% identity with TNF-R-DD) ($Fas_{DD}$, the Drosophila transcription factor bicoid, and a region of the IL-1 receptor known to be critical for signalling ($IL-1R_{477-527}$). As shown in Table 1, none of these clones interacted with TNF-R $p75_{IC}$ or $Fas_{DD}$, and only 1TU interacted with bicoid. In contrast, both 1TU and 15TU bound the cytoplasmic domain of the $p^{55}$ TNF-R, as well as residues 477–527 of the IL-1R. 27TU interacted relatively weakly with these sequences.

TABLE 1

| clone | TNF-$R_{DD}$ | TNF-R $p75_{IC}$ | TNF-R $p55_{IC}$ | $Fas_{DD}$ | bicoid | IL-1R (477–527) |
|---|---|---|---|---|---|---|
| 1TU | +++ | − | +++ | − | ++ | +++ |
| 15TU | +++ | ± | +++ | − | − | ++ |
| 27TU | +++ | − | + | − | − | + |

Interaction with Amino Acids Critical for Signalling

The ability of each clone to interact with four single-site mutations in the TNF-R death domain (each known to abolish signalling) was measured. As shown in Table 2, each of the clones interacted less strongly with the death domain mutants than with the wild type death domain, suggesting that these clones may bind critical residues in vivo.

TABLE 2

| clone | TNF-$R_{DD}$ | F345A | L351A | W378A | I408A |
|---|---|---|---|---|---|
| 1TU | +++ | + | ++ | ++ | + |
| 15TU | +++ | + | + | ++ | ++ |
| 27TU | +++ | + | + | ± | ++ |

Expression of 1TU, 15TU and 27TU

Figure 3A:
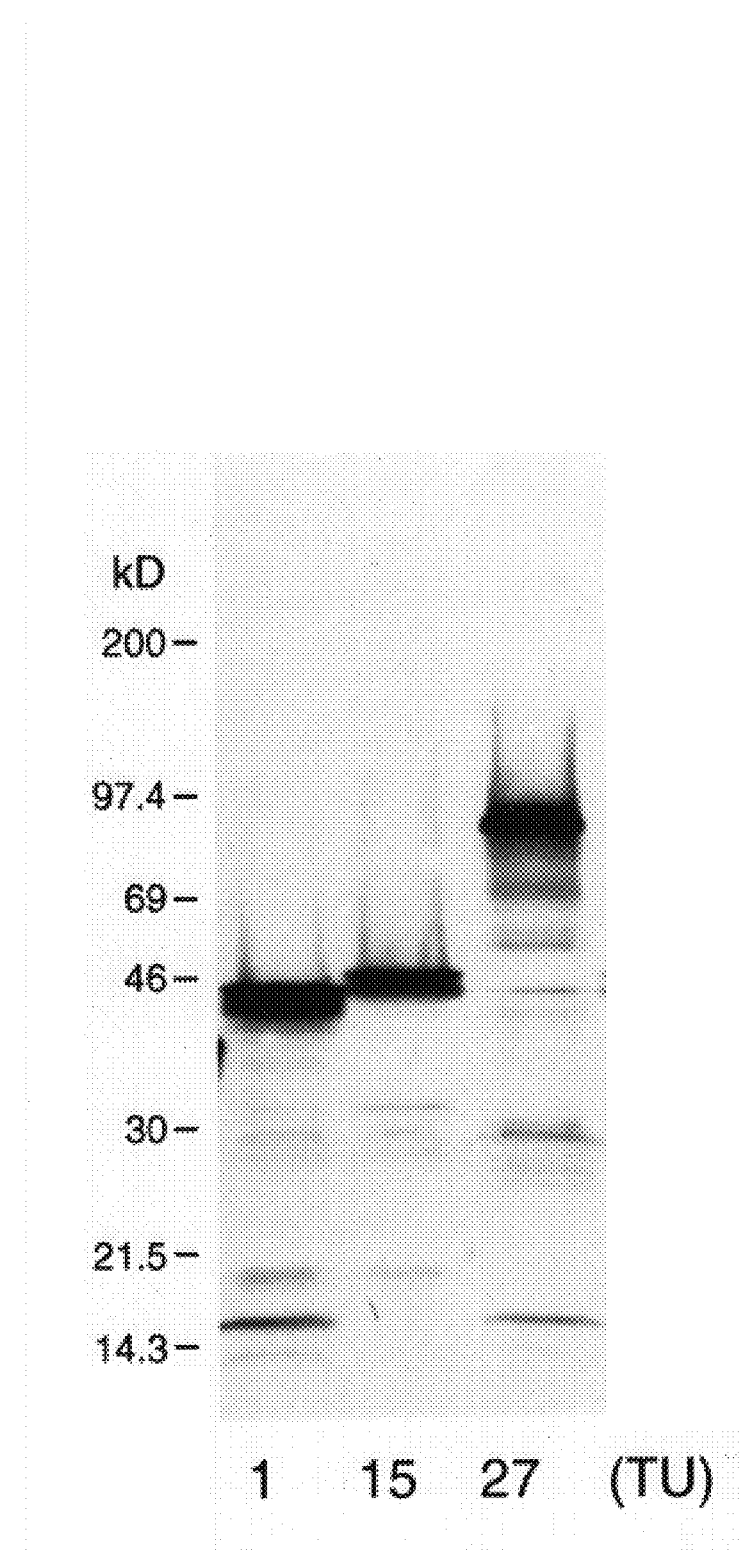
FIGS. 3A and 3B depict autoradiographs demonstrating the expression of clones 1TU, 15TU and 27TU.
Figure 3B:
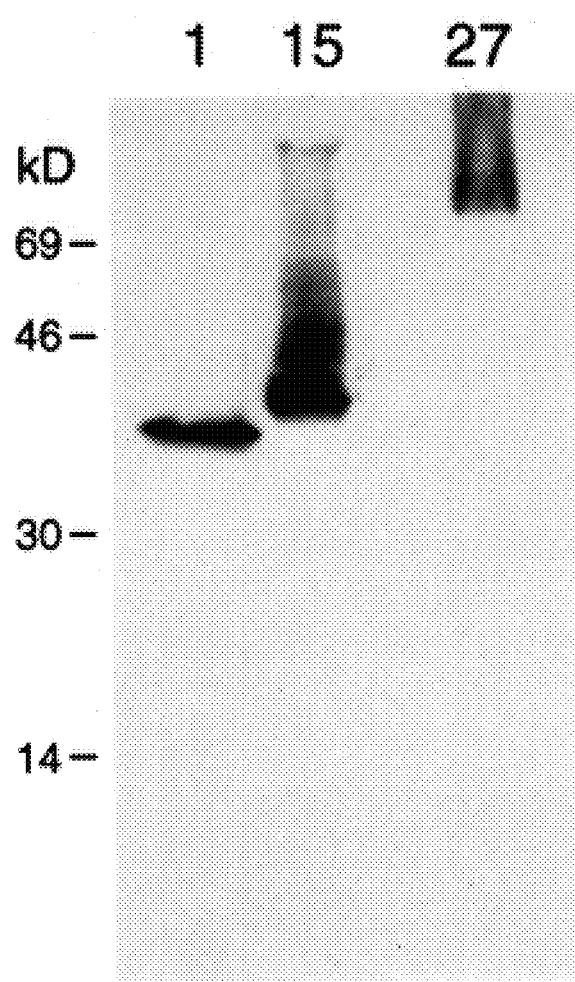

FIGS. 3A and 3B depict autoradiographs demonstrating the expression of clones 1TU, 15TU and 27TU in yeast (A) and COS cells (B).

In (A): EGY48 was transformed with pJG4–5 containing clones 1TU, 15TU or 27TU. Cells were then grown overnight in galactose/raffinose medium. Cell lysates were prepared and subjected to 4–20% SDS gel electrophoresis, followed by Western blot analysis using anti-HA antibody (12CA5, Boehringer Mannheim).

In (B): COS cells were transfected with pED-Flag containing clones 1TU, 15TU and 27TU. Cell lysates were prepared and analyzed by Western blot using anti-Flag antibody (M2, Kodak).

Specific Binding of 1TU and 27TU to TNF-R1-DD

Figure 4:
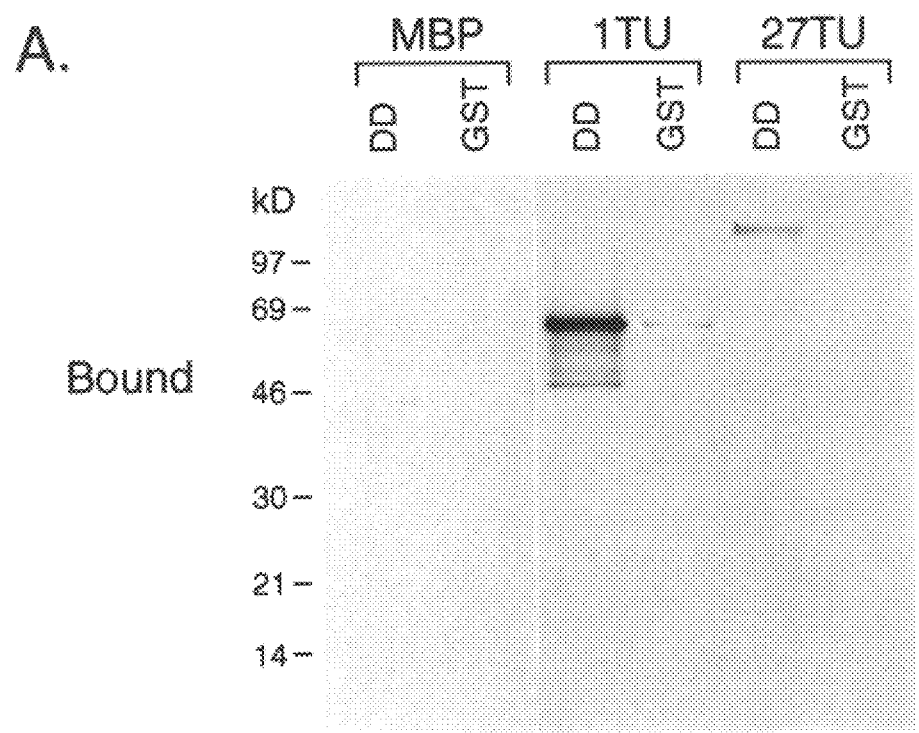
FIGS. 4A and 4B demonstrate the binding of 1TU and 27TU to TNF-R1-DD. MBP, MBP-1TU or MBP-27TU (3 µg) was incubated with glutathionie beads containing 3 µg of either GST or (GST-TNF-R1-DD in 100 µl of binding buffer (0.2% Triton, 20 mM Tris pH 7.5, 140 mM NaCl, 0.1 mM EDTA, 10 mM DTT and 5% glycerol). The reaction was performed at 4° C. for 2 hours and centrifuged to remove unbound fraction (Unbound). The beads were then washed with 500 µl binding buffer four times and resuspended into SDS-sample buffer (Bound). These samples were analyzed by Western blot using anti-MBP antibody (New England Biolab).
Figure 4:
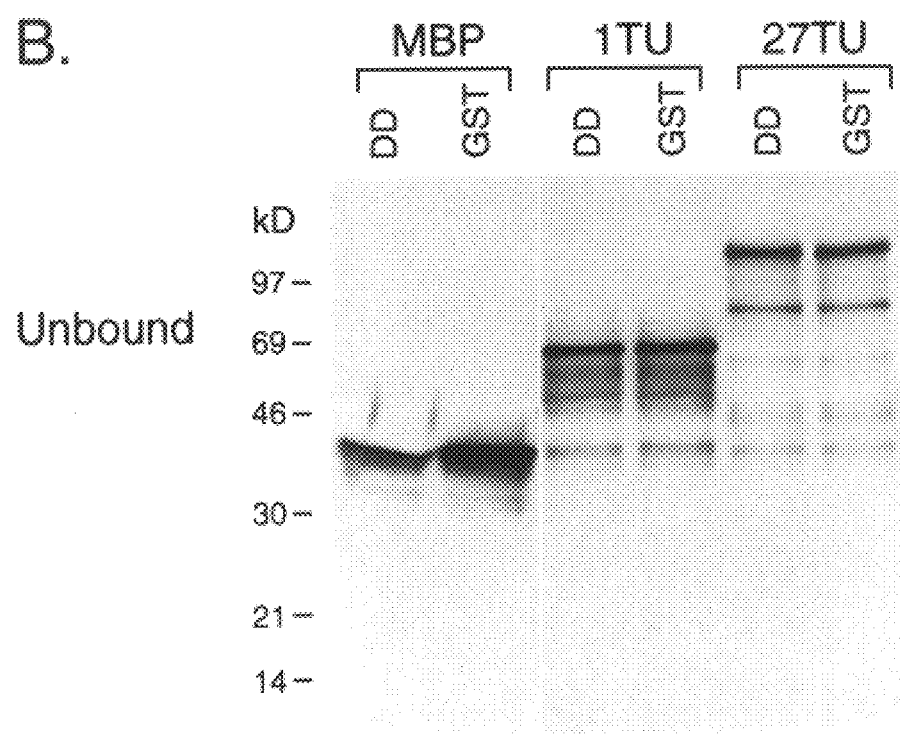

The interaction of 1TU and 27TU with TNF-R1-DD was tested using purified bacterially expressed fusion proteins. As shown in FIGS. 4A and 4B, MBP fusion proteins containing 1TU or 27TU bound only to TNF-R1-DD expressed as a GST fusion protein, but not to GST protein alone. In the control experiment, MBP protein did not bind either GST or GST/TNF-R1-DD. These results indicate that 1TU and 27TU bound specifically to the TNF-R1 death domain in vitro, confirming the data obtained in the interaction trap.

15TU and 27TU Activation of JNK Activity

Figure 5:
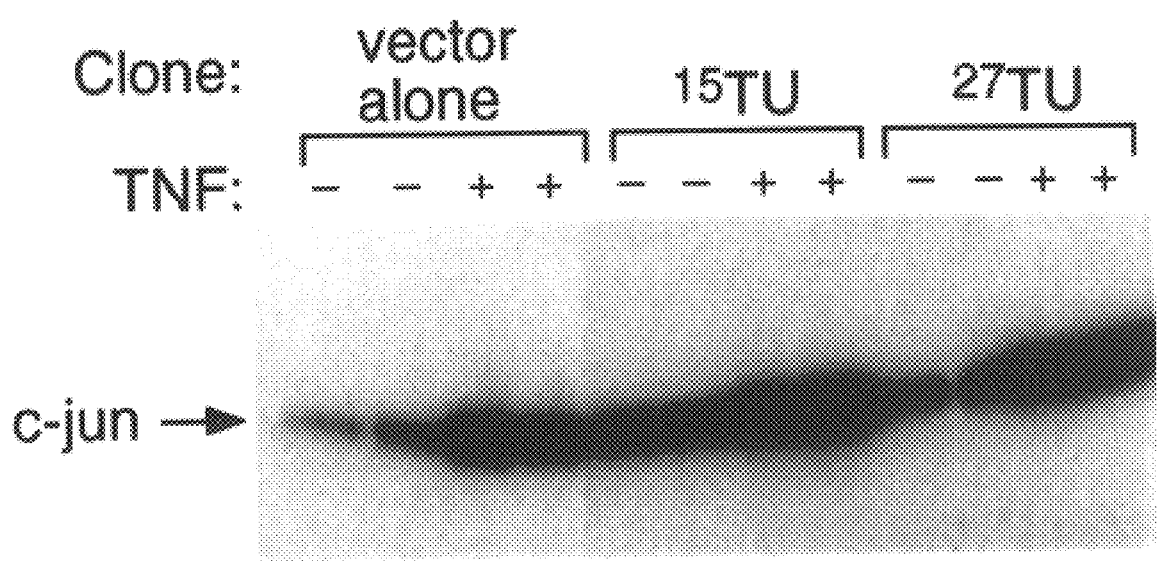
FIG. 5 demonstrates the ability of 15TU and 27TU to activate the JNK pathway. COS cells were contransfected with HA-tagged JNK1 and clones 15tu or 27TU. Cells were left untreated or treated for 15 min with 50 ng/ml TNF, and HA-JNK1 was immunoprecipitated with anti-HA antibody. JNK activity was measured in an in vitro kinase assay using GST-c-jun (amino acids 1–79) as substrate, and reactions were electrophoresed on SDS-PAGE.

The jun N-terminal kinase (JNK) is normally activated within 15 min of TNF treatment in COS cells. 15TU and 27TU were cotransfected with an epitope tagged version of JNK, HA-JNK, in duplicate. After TNF treatment, JNK was immunoprecipitated with anti-HA antibody and JNK activity was measured in immunoprecipitation kinase assays, using GST-c-jun (amino acids 1–79) as substrate). Reactions were electrophoresed on SDS-PAGE. As shown in FIG. 5, transfection of 15TU and 27TU, but not vector alone, into COS cells activated JNK even in the absence of TNF, suggesting that these clones are involved in signal transduction of TNF and the pathway leading to JNK activation in vivo.

EXAMPLE 8

ISOLATION, EXPRESSION AND ASSAY OF CLONE 3TW

Clone 3TW was isolated from the WI38 cDNA library using clone 3DD as a porbe. Clone 3TW was expressed.

Figure 6:
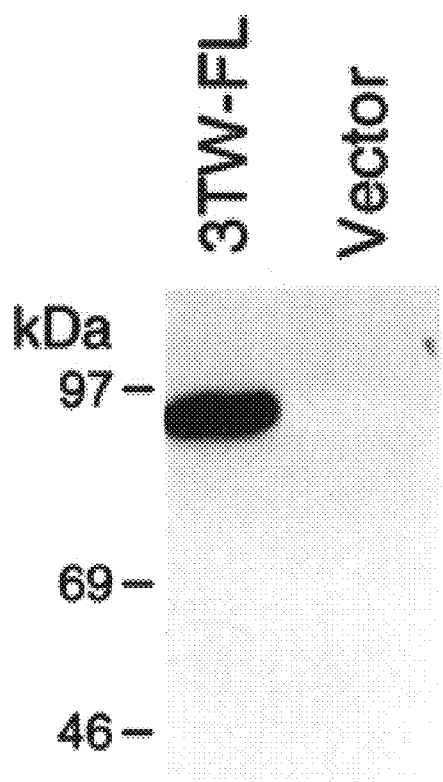
FIG. 6 is an autoradiograph of an SDS-PAGE gel of conditioned media from COS cells transfected with clone 3TW.

FIG. 6 is an autoradiograph which demonstrates expression of 3TW (indicated by arrow).

Figure 7:
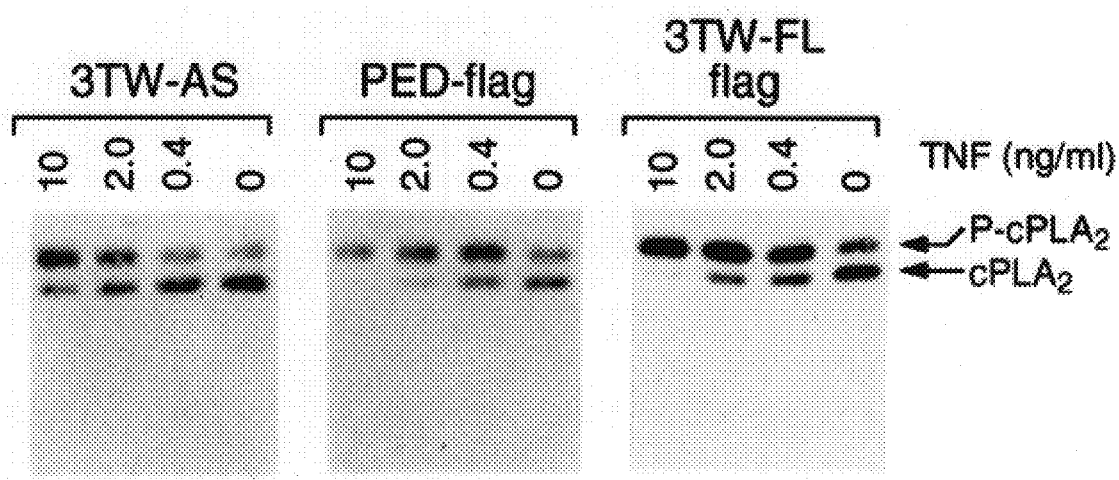
FIG. 7 is an autoradiograph which demonstrates that an antisense oligonucleotide derived from the sequence of clone 3TW inhibits TNF-induced cPLA$_2$ phosphorylation.

An antisense oligonucleotide was derived from the sequence of clone 3TW. The antisense oligonucleotide was assayed to determine its ability to inhibit TNF-induced cPLA$_2$ phosphorylation. FIG. 7 depicts the results of that experimnent. Activity of the anitsense oligonucleotide (3TWAS) was compared with the full-length clone (3TWFL), Flag-3TW full length (3TWFLflag) and pED-flag vector (pEDflag). The antisense oligonucleotide inhibited phosphorylation.

What is claimed is:

1. An isolated polynucleotide encoding a protein having TNF-R1-DD ligand activity, wherein said polynucleotide is selected from the group consisting of:
   (a) a polynucleotide comprising the nucleotide sequence of SEQ ID NO:13 from nucleotide 3 to nucleotide 2846;
   (b) a polynucleotide comprising a fragment of the nucleotide sequence of SEQ ID NO:13, the fragment comprising the nucleotide sequence of SEQ ID NO:3 from nucleotide 2 to nucleotide 415 and a nucleotide sequence not present in SEQ ID NO:3;
   (c) a polynucleotide encoding a TNF-R1-DD ligand protein comprising the amino acid sequence of SEQ ID NO:14; and
   (d) a polynucleotide encoding a TNF-R1-DD ligand protein comprising a fragment of the amino acid sequence of SEQ ID NO:14, the fragment comprising the amino acid sequence of SEQ ID NO:4 and an amino acid sequence not present in SEQ ID NO:4.

2. An isolated polynucleotide comprising the polynucleotide of claim 1 and an expression control sequence, wherein said polynucleotide of claim 1 is operably linked to said expression control sequence.

3. A host cell transformed with the polynucleotide of claim 2.

4. The host cell of claim 3, wherein said cell is a mammalian cell.

5. A process for producing a TNF-R 1-DD ligand protein encoded by the polynucleotide of claim 2, which process comprises:
   (a) growing a culture of the host cell of claim 3 in a suitable culture medium; and (b) purifying said TNF-R1-DD ligand protein from the culture.

6. An isolated polynucleotide encoding a protein having TNF-R1-DD ligand protein activity, wherein the polynucleotide is selected from the group consisting of:
  (a) a polynucleotide comprising the nucleotide sequence of SEQ ID NO:13 from nucleotide 3 to nucleotide 2846; and
  (b) a polynucleotide encoding a TNF-R1-DD ligand protein comprising the amino acid sequence of SEQ ID NO:14.

7. The polynucleotide of claim 6, wherein the polynucleotide comprises the nucleotide sequence of SEQ ID NO:13 from nucleotide 3 to nucleotide 2846.

8. The polynucleotide of claim 6, wherein the polynucleotide encodes an TNF-R1-DD ligand protein comprising the amino acid sequence of SEQ ID NO:14.

9. An isolated polynucleotide comprising the polynucleotide of claim 6 and an expression control sequence, wherein said polynucleotide of claim 6 is operably linked to said expression control sequence.

10. A host cell transformed with the polynucleotide of claim 9.

11. The host cell of claim 10, wherein said cell is a mammalian cell.

12. A process for producing a TNF-R1-DD ligand protein encoded by the polynucleotide of claim 9, which process comprises:
  (a) growing a culture of the host cell of claim 10 in a suitable culture medium; and
  (b) purifying said TNF-R1-DD ligand protein from the culture.

13. An isolated polynucleotide hybridizing in 4× SSC at 65° C. to a polynucleotide selected from the group consisting of:
  (a) a polynucleotide comprising the nucleotide sequence of SEQ ID NO:3 from nucleotide 2 to nucleotide 415;
  (b) a polynucleotide comprising a fragment of the nucleotide sequence of SEQ ID NO:3, the fragment encoding a protein having TNF-R1-DD ligand protein activity;
  (c) a polynucleotide encoding a TNF-R 1-DD ligand protein comprising the amino acid sequence of SEQ ID NO:4; and
  (d) a polynucleotide encoding a TNF-R1-DD ligand protein comprising a fragment of the amino acid sequence of SEQ ID NO:4, the fragment having TNF-R1-DD ligand protein activity.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 2158 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (ix) FEATURE:
      (A) NAME/KEY: CDS
      (B) LOCATION: 2..1231

(xi) SEQUENCE DESCRIPTION: SEQ ID NO:1:

```
C AGC AAT GCA GGT GAT GGA CCA GGT GGC GAG GGC AGT GTT CAC CTG         46
  Ser Asn Ala Gly Asp Gly Pro Gly Gly Glu Gly Ser Val His Leu
    1               5                  10                  15

GCA AGC TCT CGG GGC ACT TTG TCT GAT AGT GAA ATT GAG ACC AAC TCT        94
Ala Ser Ser Arg Gly Thr Leu Ser Asp Ser Glu Ile Glu Thr Asn Ser
                20                  25                  30

GCC ACA AGC ACC ATC TTT GGT AAA GCC CAC AGC TTG AAG CCA AGC ATA       142
Ala Thr Ser Thr Ile Phe Gly Lys Ala His Ser Leu Lys Pro Ser Ile
            35                  40                  45

AAG GAG AAG CTG GCA GGC AGC CCC ATT CGT ACT TCT GAA GAT GTG AGC       190
Lys Glu Lys Leu Ala Gly Ser Pro Ile Arg Thr Ser Glu Asp Val Ser
        50                  55                  60

CAG CGA GTC TAT CTC TAT GAG GGA CTC CTA GGC AAA GAG CGT TCT ACT       238
Gln Arg Val Tyr Leu Tyr Glu Gly Leu Leu Gly Lys Glu Arg Ser Thr
    65                  70                  75

TTA TGG GAC CAA ATG CAA TTC TGG GAA GAT GCC TTC TTA GAT GCT GTG       286
Leu Trp Asp Gln Met Gln Phe Trp Glu Asp Ala Phe Leu Asp Ala Val
 80                  85                  90                  95

ATG TTG GAG AGA GAA GGG ATG GGT ATG GAC CAG GGT CCC CAG GAA ATG       334
Met Leu Glu Arg Glu Gly Met Gly Met Asp Gln Gly Pro Gln Glu Met
                    100                 105                 110

ATC GAC AGG TAC CTG TCC CTT GGA GAA CAT GAC CGG AAG CGC CTG GAA       382
Ile Asp Arg Tyr Leu Ser Leu Gly Glu His Asp Arg Lys Arg Leu Glu
                115                 120                 125

GAT GAT GAA GAT CGC TTG CTG GCC ACA CTT CTG CAC AAC CTC ATC TCC       430
Asp Asp Glu Asp Arg Leu Leu Ala Thr Leu Leu His Asn Leu Ile Ser
            130                 135                 140

TAC ATG CTG CTG ATG AAG GTA AAT AAG AAT GAC ATC CGC AAG AAG GTG       478
Tyr Met Leu Leu Met Lys Val Asn Lys Asn Asp Ile Arg Lys Lys Val
```

```
                        145                 150                 155
AGG CGC CTA ATG GGA AAG TCG CAC ATT GGG CTT GTG TAC AGC CAG CAA             526
Arg Arg Leu Met Gly Lys Ser His Ile Gly Leu Val Tyr Ser Gln Gln
160                 165                 170                 175

ATC AAT GAG GTG CTT GAT CAG CTG GCG AAC CTG AAT GGA CGC GAT CTC             574
Ile Asn Glu Val Leu Asp Gln Leu Ala Asn Leu Asn Gly Arg Asp Leu
                180                 185                 190

TCT ATC TGG TCC AGT GGC AGC CGG CAC ATG AAG AAG CAG ACA TTT GTG             622
Ser Ile Trp Ser Ser Gly Ser Arg His Met Lys Lys Gln Thr Phe Val
            195                 200                 205

GTA CAT GCA GGG ACA GAT ACA AAC GGA GAT ATC TTT TTC ATG GAG GTG             670
Val His Ala Gly Thr Asp Thr Asn Gly Asp Ile Phe Phe Met Glu Val
        210                 215                 220

TGC GAT GAC TGT GTG GTG TTG CGT AGT AAC ATC GGA ACA GTG TAT GAG             718
Cys Asp Asp Cys Val Val Leu Arg Ser Asn Ile Gly Thr Val Tyr Glu
    225                 230                 235

CGC TGG TGG TAC GAG AAG CTC ATC AAC ATG ACC TAC TGT CCC AAG ACG             766
Arg Trp Trp Tyr Glu Lys Leu Ile Asn Met Thr Tyr Cys Pro Lys Thr
240                 245                 250                 255

AAG GTG TTG TGC TTG TGG CGT AGA AAT GGC TCT GAG ACC CAG CTC AAC             814
Lys Val Leu Cys Leu Trp Arg Arg Asn Gly Ser Glu Thr Gln Leu Asn
                260                 265                 270

AAG TTC TAT ACT AAA AAG TGT CGG GAG CTG TAC TAC TGT GTG AAG GAC             862
Lys Phe Tyr Thr Lys Lys Cys Arg Glu Leu Tyr Tyr Cys Val Lys Asp
            275                 280                 285

AGC ATG GAG CGC GCT GCC GCC CGA CAG CAA AGC ATC AAA CCC GGA CCT             910
Ser Met Glu Arg Ala Ala Ala Arg Gln Gln Ser Ile Lys Pro Gly Pro
        290                 295                 300

GAA TTG GGT GGC GAG TTC CCT GTG CAG GAC CTG AAG ACT GGT GAG GGT             958
Glu Leu Gly Gly Glu Phe Pro Val Gln Asp Leu Lys Thr Gly Glu Gly
    305                 310                 315

GGC CTG CTG CAG GTG ACC CTG GAA GGG ATC AAC CTC AAA TTC ATG CAC            1006
Gly Leu Leu Gln Val Thr Leu Glu Gly Ile Asn Leu Lys Phe Met His
320                 325                 330                 335

AAT CAG GTT TTC ATA GAG CTG AAT CAC ATT AAA AAG TGC AAT ACA GTT            1054
Asn Gln Val Phe Ile Glu Leu Asn His Ile Lys Lys Cys Asn Thr Val
                340                 345                 350

CGA GGC GTC TTT GTC CTG GAG GAA TTT GTT CCT GAA ATT AAA GAA GTG            1102
Arg Gly Val Phe Val Leu Glu Glu Phe Val Pro Glu Ile Lys Glu Val
            355                 360                 365

GTG AGC CAC AAG TAC AAG ACA CCA ATG GCC CAC GAA ATC TGC TAC TCC            1150
Val Ser His Lys Tyr Lys Thr Pro Met Ala His Glu Ile Cys Tyr Ser
        370                 375                 380

GTA TTA TGT CTC TTC TCG TAC GTG GCT GCA GTT CAT AGC AGT GAG GAA            1198
Val Leu Cys Leu Phe Ser Tyr Val Ala Ala Val His Ser Ser Glu Glu
    385                 390                 395

GAT CTC AGA ACC CCG CCC CGG CCT GTC TCT AGC TGATGGAGAG GGGCTACGCA          1251
Asp Leu Arg Thr Pro Pro Arg Pro Val Ser Ser
400                 405                 410

GCTGCCCCAG CCCAGGGCAC GCCCCTGGCC CCTTGCTGTT CCCAAGTGCA CGATGCTGCT         1311

GTGACTGAGG AGTGGATGAT GCTCGTGTGT CCTCTGCAAG CCCCCTGCTG TGGCTTGGGT         1371

GGGTACCGGT TATGTGTCCC TCTGAGTGTG TCTTGAGCGT GTCCACCTTC TCCCTCTCCA         1431

CTCCCAGAAG ACCAAACTGC CTTCCCCTCA GGGCTCAAGA ATGTGTACAG TCTGTGGGGC         1491

CGGTGTGAAC CCACTATTTT GTGTCCTTGA CACATTTGTG TTGTGGTTCC TTGTCCTTGT         1551

CCCTGGCGTT AACTGTCCAC TGCAAGAGTC TGGCTCTCCC TTCTCTGTGA CCCGGCATGA         1611

CTGGGCGCCT GGAGCAGTTT CACTCTGTGA GGAGTGAGGG AACCCTGGGG CTCACCCTCT         1671
```

```
CAGAGGAAGG GCACAGAGAG GAAGGGAAGA ATTGGGGGGC AGCCGGAGTG AGTGGCAGCC    1731

TCCCTGCTTC CTTCTGCATT CCCAAGCCGG CAGCTACTGC CCAGGGCCCG CAGTGTTGGC    1791

TGCTGCCTGC CACAGCCTCT GTGACTGCAG TGGAGCGGCG AATTCCCTGT GGCCTGCCAC    1851

GCCTTCGGCA TCAGAGGATG GAGTGGTCGA GGCTAGTGGA GTCCCAGGGA CCGCTGGCTG    1911

CTCTGCCTGA GCATCAGGGA GGGGGCAGGA AAGACCAAGC TGGGTTTGCA CATCTGTCTG    1971

CAGGCTGTCT CTCCAGGCAC GGGGTGTCAG GAGGGAGAGA CAGCCTGGGT ATGGGCAAGA    2031

AATGACTGTA AATATTTCAG CCCCACATTA TTTATAGAAA ATGTACAGTT GTGTGAATGT    2091

GAAATAAATG TCCTCACCTC CCAAAAAAAA AAAAAAAAAA AAAAAAAAAA AAAAAAAAAA    2151

AAAAAAA                                                              2158
```

(2) INFORMATION FOR SEQ ID NO:2:

(i) SEQUENCE CHARACTERISTICS:
        (A) LENGTH: 410 amino acids
        (B) TYPE: amino acid
        (D) TOPOLOGY: linear (ii) MOLECULE TYPE: protein (xi) SEQUENCE DESCRIPTION: SEQ ID NO:2:

```
Ser Asn Ala Gly Asp Gly Pro Gly Gly Glu Gly Ser Val His Leu Ala
 1               5                  10                  15

Ser Ser Arg Gly Thr Leu Ser Asp Ser Glu Ile Glu Thr Asn Ser Ala
            20                  25                  30

Thr Ser Thr Ile Phe Gly Lys Ala His Ser Leu Lys Pro Ser Ile Lys
        35                  40                  45

Glu Lys Leu Ala Gly Ser Pro Ile Arg Thr Ser Glu Asp Val Ser Gln
    50                  55                  60

Arg Val Tyr Leu Tyr Glu Gly Leu Leu Gly Lys Glu Arg Ser Thr Leu
65                  70                  75                  80

Trp Asp Gln Met Gln Phe Trp Glu Asp Ala Phe Leu Asp Ala Val Met
                85                  90                  95

Leu Glu Arg Glu Gly Met Gly Met Asp Gln Gly Pro Gln Glu Met Ile
            100                 105                 110

Asp Arg Tyr Leu Ser Leu Gly Glu His Asp Arg Lys Arg Leu Glu Asp
        115                 120                 125

Asp Glu Asp Arg Leu Leu Ala Thr Leu Leu His Asn Leu Ile Ser Tyr
    130                 135                 140

Met Leu Leu Met Lys Val Asn Lys Asn Asp Ile Arg Lys Lys Val Arg
145                 150                 155                 160

Arg Leu Met Gly Lys Ser His Ile Gly Leu Val Tyr Ser Gln Gln Ile
                165                 170                 175

Asn Glu Val Leu Asp Gln Leu Ala Asn Leu Asn Gly Arg Asp Leu Ser
            180                 185                 190

Ile Trp Ser Ser Gly Ser Arg His Met Lys Lys Gln Thr Phe Val Val
        195                 200                 205

His Ala Gly Thr Asp Thr Asn Gly Asp Ile Phe Phe Met Glu Val Cys
    210                 215                 220

Asp Asp Cys Val Val Leu Arg Ser Asn Ile Gly Thr Val Tyr Glu Arg
225                 230                 235                 240

Trp Trp Tyr Glu Lys Leu Ile Asn Met Thr Tyr Cys Pro Lys Thr Lys
                245                 250                 255

Val Leu Cys Leu Trp Arg Arg Asn Gly Ser Glu Thr Gln Leu Asn Lys
            260                 265                 270
```

```
Phe Tyr Thr Lys Lys Cys Arg Glu Leu Tyr Tyr Cys Val Lys Asp Ser
            275                 280                 285

Met Glu Arg Ala Ala Arg Gln Gln Ser Ile Lys Pro Gly Pro Glu
    290                 295                 300

Leu Gly Gly Glu Phe Pro Val Gln Asp Leu Lys Thr Gly Glu Gly Gly
305                 310                 315                 320

Leu Leu Gln Val Thr Leu Glu Gly Ile Asn Leu Lys Phe Met His Asn
                325                 330                 335

Gln Val Phe Ile Glu Leu Asn His Ile Lys Lys Cys Asn Thr Val Arg
                340                 345                 350

Gly Val Phe Val Leu Glu Glu Phe Val Pro Glu Ile Lys Glu Val Val
            355                 360                 365

Ser His Lys Tyr Lys Thr Pro Met Ala His Glu Ile Cys Tyr Ser Val
    370                 375                 380

Leu Cys Leu Phe Ser Tyr Val Ala Ala Val His Ser Ser Glu Glu Asp
385                 390                 395                 400

Leu Arg Thr Pro Pro Arg Pro Val Ser Ser
                405                 410

(2) INFORMATION FOR SEQ ID NO:3:

(i) SEQUENCE CHARACTERISTICS:
        (A) LENGTH: 826 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 2..415

(xi) SEQUENCE DESCRIPTION: SEQ ID NO:3:

G GAG GTG CAG GAC CTC TTC GAA GCC CAG GGC AAT GAC CGA CTG AAG        46
  Glu Val Gln Asp Leu Phe Glu Ala Gln Gly Asn Asp Arg Leu Lys
  1               5                   10                  15

CTG CTG GTG CTG TAC AGT GGA GAG GAT GAT GAG CTG CTA CAG CGG GCA     94
Leu Leu Val Leu Tyr Ser Gly Glu Asp Asp Glu Leu Leu Gln Arg Ala
                20                  25                  30

GCT GCC GGG GGC TTG GCC ATG CTT ACC TCC ATG CGG CCC ACG CTC TGC     142
Ala Ala Gly Gly Leu Ala Met Leu Thr Ser Met Arg Pro Thr Leu Cys
            35                  40                  45

AGC CGC ATT CCC CAA GTG ACC ACA CAC TGG CTG GAG ATC CTG CAG GCC     190
Ser Arg Ile Pro Gln Val Thr Thr His Trp Leu Glu Ile Leu Gln Ala
        50                  55                  60

CTG CTT CTG AGC TCC AAC CAG GAG CTG CAG CAC CGG GGT GCT GTG GTG     238
Leu Leu Leu Ser Ser Asn Gln Glu Leu Gln His Arg Gly Ala Val Val
    65                  70                  75

GTG CTG AAC ATG GTG GAG GCC TCG AGG GAG ATT GCC AGC ACC CTG ATG     286
Val Leu Asn Met Val Glu Ala Ser Arg Glu Ile Ala Ser Thr Leu Met
80                  85                  90                  95

GAG AGT GAG ATG ATG GAG ATC TTG TCA GTG CTA GCT AAG GGT GAC CAC     334
Glu Ser Glu Met Met Glu Ile Leu Ser Val Leu Ala Lys Gly Asp His
                100                 105                 110

AGC CCT GTC ACA AGG GCT GCT GCA GCC TGC CTG GAC AAA GCA GTG GAA     382
Ser Pro Val Thr Arg Ala Ala Ala Ala Cys Leu Asp Lys Ala Val Glu
            115                 120                 125

TAT GGG CTT ATC CAA CCC AAC CAA GAT GGA GAG TGAGGGGGTT GTCCCTGGGC   435
```

Tyr Gly Leu Ile Gln Pro Asn Gln Asp Gly Glu
        130                 135

CCAAGGCTCA TGCACACGCT ACCTATTGTG GCACGGAGAG TAAGGACGGA AGCAGCTTTG    495

GCTGGTGGTG GCTGGCATGC CCAATACTCT TGCCCATCCT CGCTTGCTGC CCTAGGATGT    555

CCTCTGTTCT GAGTCAGCGG CCACGTTCAG TCACACAGCC CTGCTTGGCC AGCACTGCCT    615

GCAGCCTCAC TCAGAGGGGC CCTTTTTCTG TACTACTGTA GTCAGCTGGG AATGGGGAAG    675

GTGCATCCCA ACACAGCCTG TGGATCCTGG GGCATTTGGA AGGGCGCACA CATCAGCAGC    735

CTCACCAGCT GTGAGCCTGC TATCAGGCCT GCCCCTCCAA TAAAAGTGTG TAGAACTCCA    795

AAAAAAAAAA AAAAAAAAAA AAAAAAAAA A                                    826

(2) INFORMATION FOR SEQ ID NO:4:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO:4:

Glu Val Gln Asp Leu Phe Glu Ala Gln Gly Asn Asp Arg Leu Lys Leu
 1               5                  10                  15

Leu Val Leu Tyr Ser Gly Glu Asp Asp Glu Leu Leu Gln Arg Ala Ala
            20                  25                  30

Ala Gly Gly Leu Ala Met Leu Thr Ser Met Arg Pro Thr Leu Cys Ser
        35                  40                  45

Arg Ile Pro Gln Val Thr Thr His Trp Leu Glu Ile Leu Gln Ala Leu
    50                  55                  60

Leu Leu Ser Ser Asn Gln Glu Leu Gln His Arg Gly Ala Val Val Val
65                  70                  75                  80

Leu Asn Met Val Glu Ala Ser Arg Glu Ile Ala Ser Thr Leu Met Glu
                85                  90                  95

Ser Glu Met Met Glu Ile Leu Ser Val Leu Ala Lys Gly Asp His Ser
            100                 105                 110

Pro Val Thr Arg Ala Ala Ala Ala Cys Leu Asp Lys Ala Val Glu Tyr
        115                 120                 125

Gly Leu Ile Gln Pro Asn Gln Asp Gly Glu
    130                 135

(2) INFORMATION FOR SEQ ID NO:5:

(i) SEQUENCE CHARACTERISTICS:
        (A) LENGTH: 722 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 2..559

(xi) SEQUENCE DESCRIPTION: SEQ ID NO:5:

G GAG AAG CCG CTG CAC GCC CTG CTG CAC GGC CGC GGG GTT TGC CTC         46
  Glu Lys Pro Leu His Ala Leu Leu His Gly Arg Gly Val Cys Leu
   1               5                  10                  15

AAC GAA AAG AGC TAC CGC GAG CAA GTC AAG ATC GAG AGA GAC TCC CGT       94

```
Asn Glu Lys Ser Tyr Arg Glu Gln Val Lys Ile Glu Arg Asp Ser Arg
            20                  25                  30

GAG CAC GAG GAG CCC ACC ACC TCT GAG ATG GCC GAG GAG ACC TAC TCC    142
Glu His Glu Glu Pro Thr Thr Ser Glu Met Ala Glu Glu Thr Tyr Ser
            35                  40                  45

CCC AAG ATC TTC CGG CCC AAA CAC ACC CGC ATC TCC GAG CTG AAG GCT    190
Pro Lys Ile Phe Arg Pro Lys His Thr Arg Ile Ser Glu Leu Lys Ala
            50                  55                  60

GAA GCA GTG AAG AAG GAC CGC AGA AAG AAG CTG ACC CAG TCC AAG TTT    238
Glu Ala Val Lys Lys Asp Arg Arg Lys Lys Leu Thr Gln Ser Lys Phe
65                  70                  75

GTC GGG GGA GCC GAG AAC ACT GCC CAC CCC CGG ATC ATC TCT GAA CCT    286
Val Gly Gly Ala Glu Asn Thr Ala His Pro Arg Ile Ile Ser Glu Pro
    80                  85                  90                  95

GAG ATG AGA CAG GAG TCT GAG CAG GGC CCC TGC CGC AGA CAC ATG GAG    334
Glu Met Arg Gln Glu Ser Glu Gln Gly Pro Cys Arg Arg His Met Glu
                100                 105                 110

GCT TCC CTG CAG GAG CTC AAA GCC AGC CCA CGC ATG GTG CCC CGT GCT    382
Ala Ser Leu Gln Glu Leu Lys Ala Ser Pro Arg Met Val Pro Arg Ala
            115                 120                 125

GTG TAC CTG CCC AAT TGT GAC CGC AAA GGA TTC TAC AAG AGA AAG CAG    430
Val Tyr Leu Pro Asn Cys Asp Arg Lys Gly Phe Tyr Lys Arg Lys Gln
        130                 135                 140

TGC AAA CCT TCC CGT GGC CGC AAG CGT GGC ATC TGC TGG TGC GTG GAC    478
Cys Lys Pro Ser Arg Gly Arg Lys Arg Gly Ile Cys Trp Cys Val Asp
    145                 150                 155

AAG TAC GGG ATG AAG CTG CCA GGC ATG GAG TAC GTT GAC GGG GAC TTT    526
Lys Tyr Gly Met Lys Leu Pro Gly Met Glu Tyr Val Asp Gly Asp Phe
160                 165                 170                 175

CAG TGC CAC ACC TTC GAC AGC AGC AAC GTT GAG TGATGCGTCC CCCCCCAACC  579
Gln Cys His Thr Phe Asp Ser Ser Asn Val Glu
                180                 185

TTTCCCTCAC CCCCTTCCAC CCCCAGCCCC GACTCCAGCC AGCGCCTCCC TCCACCCCAG  639

GACGCCACTC ATTTCATCTC ATTTAAGGGA AAAATATATA TCTATCTATT TGAGGAAAAA  699

AAAAAAAAAA AAAAAAAAAA AAA                                         722

(2) INFORMATION FOR SEQ ID NO:6:

(i) SEQUENCE CHARACTERISTICS:
        (A) LENGTH: 186 amino acids
        (B) TYPE: amino acid
        (D) TOPOLOGY: linear (ii) MOLECULE TYPE: protein (xi) SEQUENCE DESCRIPTION: SEQ ID NO:6:

Glu Lys Pro Leu His Ala Leu Leu His Gly Arg Gly Val Cys Leu Asn
1               5                   10                  15

Glu Lys Ser Tyr Arg Glu Gln Val Lys Ile Glu Arg Asp Ser Arg Glu
            20                  25                  30

His Glu Glu Pro Thr Thr Ser Glu Met Ala Glu Glu Thr Tyr Ser Pro
        35                  40                  45

Lys Ile Phe Arg Pro Lys His Thr Arg Ile Ser Glu Leu Lys Ala Glu
    50                  55                  60

Ala Val Lys Lys Asp Arg Arg Lys Lys Leu Thr Gln Ser Lys Phe Val
65                  70                  75                  80

Gly Gly Ala Glu Asn Thr Ala His Pro Arg Ile Ile Ser Glu Pro Glu
                85                  90                  95

Met Arg Gln Glu Ser Glu Gln Gly Pro Cys Arg Arg His Met Glu Ala
```

100                 105                 110
Ser Leu Gln Glu Leu Lys Ala Ser Pro Arg Met Val Pro Arg Ala Val
        115                 120                 125

Tyr Leu Pro Asn Cys Asp Arg Lys Gly Phe Tyr Lys Arg Lys Gln Cys
    130                 135                 140

Lys Pro Ser Arg Gly Arg Lys Arg Gly Ile Cys Trp Cys Val Asp Lys
145                 150                 155                 160

Tyr Gly Met Lys Leu Pro Gly Met Glu Tyr Val Asp Gly Asp Phe Gln
                165                 170                 175

Cys His Thr Phe Asp Ser Ser Asn Val Glu
                180                 185

(2) INFORMATION FOR SEQ ID NO:7:

(i) SEQUENCE CHARACTERISTICS:
        (A) LENGTH: 1023 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 57..875

(xi) SEQUENCE DESCRIPTION: SEQ ID NO:7:

CCCTGCACTC TCGCTCTCCT GCCCCACCCC GAGGTAAAGG GGGCGACTAA GAGAAG                56

ATG GTG TTG CTC ACC GCG GTC CTC CTG CTG CTG GCC GCC TAT GCG GGG           104
Met Val Leu Leu Thr Ala Val Leu Leu Leu Leu Ala Ala Tyr Ala Gly
 1               5                  10                  15

CCG GCC CAG AGC CTG GGC TCC TTC GTG CAC TGC GAG CCC TGC GAC GAG           152
Pro Ala Gln Ser Leu Gly Ser Phe Val His Cys Glu Pro Cys Asp Glu
                20                  25                  30

AAA GCC CTC TCC ATG TGC CCC CCC AGC CCC CTG GGC TGC GAG CTG GTC           200
Lys Ala Leu Ser Met Cys Pro Pro Ser Pro Leu Gly Cys Glu Leu Val
         35                  40                  45

AAG GAG CCG GGC TGC GGC TGC TGC ATG ACC TGC GCC CTG GCC GAG GGG           248
Lys Glu Pro Gly Cys Gly Cys Cys Met Thr Cys Ala Leu Ala Glu Gly
 50                  55                  60

CAG TCG TGC GGC GTC TAC ACC GAG CGC TGC GCC CAG GGG CTG CGC TGC           296
Gln Ser Cys Gly Val Tyr Thr Glu Arg Cys Ala Gln Gly Leu Arg Cys
 65                  70                  75                  80

CTC CCC CGG CAG GAC GAG GAG AAG CCG CTG CAC GCC CTG CTG CAC GGC           344
Leu Pro Arg Gln Asp Glu Glu Lys Pro Leu His Ala Leu Leu His Gly
                85                  90                  95

CGC GGG GTT TGC CTC AAC GAA AAG AGC TAC CGC GAG CAA GTC AAG ATC           392
Arg Gly Val Cys Leu Asn Glu Lys Ser Tyr Arg Glu Gln Val Lys Ile
                100                 105                 110

GAG AGA GAC TCC CGT GAG CAC GAG GAG CCC ACC ACC TCT GAG ATG GCC           440
Glu Arg Asp Ser Arg Glu His Glu Glu Pro Thr Thr Ser Glu Met Ala
        115                 120                 125

GAG GAG ACC TAC TCC CCC AAG ATC TTC CGG CCC AAA CAC ACC CGC ATC           488
Glu Glu Thr Tyr Ser Pro Lys Ile Phe Arg Pro Lys His Thr Arg Ile
        130                 135                 140

TCC GAG CTG AAG GCT GAA GCA GTG AAG AAG GAC CGC AGA AAG AAG CTG           536
Ser Glu Leu Lys Ala Glu Ala Val Lys Lys Asp Arg Arg Lys Lys Leu
145                 150                 155                 160

ACC CAG TCC AAG TTT GTC GGG GGA GCC GAG AAC ACT GCC CAC CCC CGG           584
Thr Gln Ser Lys Phe Val Gly Gly Ala Glu Asn Thr Ala His Pro Arg

```
            165                 170                 175
ATC ATC TCT GCA CCT GAG ATG AGA CAG GAG TCT GAG CAG GGC CCC TGC       632
Ile Ile Ser Ala Pro Glu Met Arg Gln Glu Ser Glu Gln Gly Pro Cys
            180                 185                 190

CGC AGA CAC ATG GAG GCT TCC CTG CAG GAG CTC AAA GCC AGC CCA CGC       680
Arg Arg His Met Glu Ala Ser Leu Gln Glu Leu Lys Ala Ser Pro Arg
            195                 200                 205

ATG GTG CCC CGT GCT GTG TAC CTG CCC AAT TGT GAC CGC AAA GGA TTC       728
Met Val Pro Arg Ala Val Tyr Leu Pro Asn Cys Asp Arg Lys Gly Phe
            210                 215                 220

TAC AAG AGA AAG CAG TGC AAA CCT TCC CGT GGC CGC AAG CGT GGC ATC       776
Tyr Lys Arg Lys Gln Cys Lys Pro Ser Arg Gly Arg Lys Arg Gly Ile
225                 230                 235                 240

TGC TGG TGC GTG GAC AAG TAC GGG ATG AAG CTG CCA GGC ATG GAG TAC       824
Cys Trp Cys Val Asp Lys Tyr Gly Met Lys Leu Pro Gly Met Glu Tyr
                    245                 250                 255

GTT GAC GGG GAC TTT CAG TGC CAC ACC TTC GAC AGC AGC AAC GTT GAG       872
Val Asp Gly Asp Phe Gln Cys His Thr Phe Asp Ser Ser Asn Val Glu
                260                 265                 270

TGATGCGTCC CCCCCAACC TTTCCCTCAC CCCCTCCCAC CCCCAGCCCC GACTCCAGCC      932

AGCGCCTCCC TCCACCCCAG GACGCCACTC ATTTCATCTC ATTTAAGGGA AAAATATATA     992

TCTATCTATT TGAAAAAAAA AAAAAAACC C                                    1023

(2) INFORMATION FOR SEQ ID NO:8:

(i) SEQUENCE CHARACTERISTICS:
        (A) LENGTH: 272 amino acids
        (B) TYPE: amino acid
        (D) TOPOLOGY: linear (ii) MOLECULE TYPE: protein (xi) SEQUENCE DESCRIPTION: SEQ ID NO:8:

Met Val Leu Leu Thr Ala Val Leu Leu Leu Ala Ala Tyr Ala Gly
 1               5                  10                  15

Pro Ala Gln Ser Leu Gly Ser Phe Val His Cys Glu Pro Cys Asp Glu
            20                  25                  30

Lys Ala Leu Ser Met Cys Pro Pro Ser Pro Leu Gly Cys Glu Leu Val
         35                  40                  45

Lys Glu Pro Gly Cys Gly Cys Cys Met Thr Cys Ala Leu Ala Glu Gly
      50                  55                  60

Gln Ser Cys Gly Val Tyr Thr Glu Arg Cys Ala Gln Gly Leu Arg Cys
65                  70                  75                  80

Leu Pro Arg Gln Asp Glu Glu Lys Pro Leu His Ala Leu Leu His Gly
                85                  90                  95

Arg Gly Val Cys Leu Asn Glu Lys Ser Tyr Arg Glu Gln Val Lys Ile
            100                 105                 110

Glu Arg Asp Ser Arg Glu His Glu Glu Pro Thr Thr Ser Glu Met Ala
         115                 120                 125

Glu Glu Thr Tyr Ser Pro Lys Ile Phe Arg Pro Lys His Thr Arg Ile
      130                 135                 140

Ser Glu Leu Lys Ala Glu Ala Val Lys Lys Asp Arg Arg Lys Lys Leu
145                 150                 155                 160

Thr Gln Ser Lys Phe Val Gly Gly Ala Glu Asn Thr Ala His Pro Arg
                165                 170                 175

Ile Ile Ser Ala Pro Glu Met Arg Gln Glu Ser Glu Gln Gly Pro Cys
            180                 185                 190
```

```
Arg Arg His Met Glu Ala Ser Leu Gln Glu Leu Lys Ala Ser Pro Arg
        195                 200                 205

Met Val Pro Arg Ala Val Tyr Leu Pro Asn Cys Asp Arg Lys Gly Phe
    210                 215                 220

Tyr Lys Arg Lys Gln Cys Lys Pro Ser Arg Gly Arg Lys Arg Gly Ile
225                 230                 235                 240

Cys Trp Cys Val Asp Lys Tyr Gly Met Lys Leu Pro Gly Met Glu Tyr
                245                 250                 255

Val Asp Gly Asp Phe Gln Cys His Thr Phe Asp Ser Ser Asn Val Glu
                260                 265                 270
```

(2) INFORMATION FOR SEQ ID NO:9:

(i) SEQUENCE CHARACTERISTICS:
        (A) LENGTH: 1694 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 2..931

(xi) SEQUENCE DESCRIPTION: SEQ ID NO:9:

```
C TCT CTC AAG GCC AAC ATC CCT GAG GTG GAA GCT GTC CTC AAC ACC           46
  Ser Leu Lys Ala Asn Ile Pro Glu Val Glu Ala Val Leu Asn Thr
  1               5                  10                  15

GAC AGG AGT TTG GTG TGT GAT GGG AAG AGG GGC TTA TTA ACT CGT CTG         94
Asp Arg Ser Leu Val Cys Asp Gly Lys Arg Gly Leu Leu Thr Arg Leu
              20                  25                  30

CTG CAG GTC ATG AAG AAG GAG CCA GCA GAG TCG TCT TTC AGG TTT TGG        142
Leu Gln Val Met Lys Lys Glu Pro Ala Glu Ser Ser Phe Arg Phe Trp
          35                  40                  45

CAA GCT CGG GCT GTG GAG AGT TTC CTC CGA GGG ACC ACC TCC TAT GCA        190
Gln Ala Arg Ala Val Glu Ser Phe Leu Arg Gly Thr Thr Ser Tyr Ala
      50                  55                  60

GAC CAG ATG TTC CTG CTG AAG CGA GGC CTC TTG GAG CAC ATC CTT TAC        238
Asp Gln Met Phe Leu Leu Lys Arg Gly Leu Leu Glu His Ile Leu Tyr
  65                  70                  75

TGC ATT GTG GAC AGC GAG TGT AAG TCA AGG GAT GTG CTC CAG AGT TAC        286
Cys Ile Val Asp Ser Glu Cys Lys Ser Arg Asp Val Leu Gln Ser Tyr
80                  85                  90                  95

TTT GAC CTC CTG GGG GAG CTG ATG AAG TTC AAC GTT GAT GCA TTC AAG        334
Phe Asp Leu Leu Gly Glu Leu Met Lys Phe Asn Val Asp Ala Phe Lys
                100                 105                 110

AGA TTC AAT AAA TAT ATC AAC ACC GAT GCA AAG TTC CAG GTA TTC CTG        382
Arg Phe Asn Lys Tyr Ile Asn Thr Asp Ala Lys Phe Gln Val Phe Leu
            115                 120                 125

AAG CAG ATC AAC AGC TCC CTG GTG GAC TCC AAC ATG CTG GTG CGC TGT        430
Lys Gln Ile Asn Ser Ser Leu Val Asp Ser Asn Met Leu Val Arg Cys
        130                 135                 140

GTC ACT CTG TCC CTG GAC CGA TTT GAA AAC CAG GTG GAT ATG AAA GTT        478
Val Thr Leu Ser Leu Asp Arg Phe Glu Asn Gln Val Asp Met Lys Val
    145                 150                 155

GCC GAG GTA CTG TCT GAA TGC CGC CTG CTC GCC TAC ATA TCC CAG GTG        526
Ala Glu Val Leu Ser Glu Cys Arg Leu Leu Ala Tyr Ile Ser Gln Val
160                 165                 170                 175

CCC ACG CAG ATG TCC TTC CTC TTC CGC CTC ATC AAC ATC ATC CAC GTG        574
Pro Thr Gln Met Ser Phe Leu Phe Arg Leu Ile Asn Ile Ile His Val
```

```
                                 180                    185                   190
CAG ACG CTG ACC CAG GAG AAC GTC AGC TGC CTC AAC ACC AGC CTG GTG              622
Gln Thr Leu Thr Gln Glu Asn Val Ser Cys Leu Asn Thr Ser Leu Val
        195                  200                  205

ATC CTG ATG CTG GCC CGA CGG AAA GAG CGG CTG CCC CTG TAC CTG CGG              670
Ile Leu Met Leu Ala Arg Arg Lys Glu Arg Leu Pro Leu Tyr Leu Arg
        210                  215                  220

CTG CTG CAG CGG ATG GAG CAC AGC AAG AAG TAC CCC GGC TTC CTG CTC              718
Leu Leu Gln Arg Met Glu His Ser Lys Lys Tyr Pro Gly Phe Leu Leu
        225                  230                  235

AAC AAC TTC CAC AAC CTG CTG CGC TTC TGG CAG CAG CAC TAC CTG CAC              766
Asn Asn Phe His Asn Leu Leu Arg Phe Trp Gln Gln His Tyr Leu His
240                  245                  250                  255

AAG GAC AAG GAC AGC ACC TGC CTA GAG AAC AGC TCC TGC ATC AGC TTC              814
Lys Asp Lys Asp Ser Thr Cys Leu Glu Asn Ser Ser Cys Ile Ser Phe
                260                  265                  270

TCA TAC TGG AAG GAG ACA GTG TCC ATC CTG TTG AAC CCG GAC CGG CAG              862
Ser Tyr Trp Lys Glu Thr Val Ser Ile Leu Leu Asn Pro Asp Arg Gln
                275                  280                  285

TCA CCC TCT GCT CTC GTT AGC TAC ATT GAG GAG CCC TAC ATG GAC ATA              910
Ser Pro Ser Ala Leu Val Ser Tyr Ile Glu Glu Pro Tyr Met Asp Ile
                290                  295                  300

GAC AGG GAC TTC ACT GAG GAG TGACCTTGGG CCAGGCCTCG GGAGGCTGCT                 961
Asp Arg Asp Phe Thr Glu Glu
                305                  310

GGGCCAGTGT GGGTGAGCGT GGGTACGATG CCACACGCCC TGCCCTGTTC CCGTTCCTCC           1021

CTGCTGCTCT CTGCCTGCCC CAGGTCTTTG GGTACAGGCT TGGTGGGAGG GAAGTCCTAG           1081

AAGCCCTTGG TCCCCCTGGG TCTGAGGGCC CTAGGTCATG GAGAGCCTCA GTCCCCATAA           1141

TGAGGACAGG GTACCATGCC CACCTTTCCT TCAGAACCCT GGGGCCCAGG GCCACCCAGA           1201

GGTAAGAGGA CATTTAGCAT TAGCTCTGTG TGAGCTCCTG CCGGTTTCTT GGCTGTCAGT           1261

CAGTCCCAGA GTGGGAGGA AGATATGGGT GACCCCCACC CCCCATCTGT GAGCCAAGCC            1321

TCCCTTGTCC CTGGCCTTTG GACCCAGGCA AAGGCTTCTG AGCCCTGGGC AGGGGTGGTG           1381

GGTACCAGAG AATGCTGCCT TCCCCCAAGC CTGCCCCTCT GCCTCATTTT CCTGTAGCTC           1441

CTCTGGTTCT GTTTGCTCAT TGGCCGCTGT GTTCATCCAA GGGGGTTCTC CCAGAAGTGA           1501

GGGGCCTTTC CCTCCATCCC TTGGGGCACG GGGCAGCTGT GCCTGCCCTG CCTCTGCCTG           1561

AGGCAGCCGC TCCTGCCTGA GCCTGGACAT GGGGCCCTTC CTTGTGTTGC CAATTTATTA           1621

ACAGCAAATA AACCAATTAA ATGGAGACTA TTAAATAACT TTATTTTAAA AATGAAAAAA           1681

AAAAAAAAAA AAA                                                             1694

(2) INFORMATION FOR SEQ ID NO:10:

(i) SEQUENCE CHARACTERISTICS:
        (A) LENGTH: 310 amino acids
        (B) TYPE: amino acid
        (D) TOPOLOGY: linear (ii) MOLECULE TYPE: protein (xi) SEQUENCE DESCRIPTION: SEQ ID NO:10:

Ser Leu Lys Ala Asn Ile Pro Glu Val Glu Ala Val Leu Asn Thr Asp
 1               5                  10                  15

Arg Ser Leu Val Cys Asp Gly Lys Arg Gly Leu Leu Thr Arg Leu Leu
                20                  25                  30

Gln Val Met Lys Lys Glu Pro Ala Glu Ser Ser Phe Arg Phe Trp Gln
            35                  40                  45
```

```
Ala Arg Ala Val Glu Ser Phe Leu Arg Gly Thr Thr Ser Tyr Ala Asp
         50                  55                  60

Gln Met Phe Leu Leu Lys Arg Gly Leu Leu Glu His Ile Leu Tyr Cys
 65                  70                  75                  80

Ile Val Asp Ser Glu Cys Lys Ser Arg Asp Val Leu Gln Ser Tyr Phe
                 85                  90                  95

Asp Leu Leu Gly Glu Leu Met Lys Phe Asn Val Asp Ala Phe Lys Arg
             100                 105                 110

Phe Asn Lys Tyr Ile Asn Thr Asp Ala Lys Phe Gln Val Phe Leu Lys
         115                 120                 125

Gln Ile Asn Ser Ser Leu Val Asp Ser Asn Met Leu Val Arg Cys Val
130                 135                 140

Thr Leu Ser Leu Asp Arg Phe Glu Asn Gln Val Asp Met Lys Val Ala
145                 150                 155                 160

Glu Val Leu Ser Glu Cys Arg Leu Leu Ala Tyr Ile Ser Gln Val Pro
                 165                 170                 175

Thr Gln Met Ser Phe Leu Phe Arg Leu Ile Asn Ile Ile His Val Gln
             180                 185                 190

Thr Leu Thr Gln Glu Asn Val Ser Cys Leu Asn Thr Ser Leu Val Ile
         195                 200                 205

Leu Met Leu Ala Arg Arg Lys Glu Arg Leu Pro Leu Tyr Leu Arg Leu
210                 215                 220

Leu Gln Arg Met Glu His Ser Lys Lys Tyr Pro Gly Phe Leu Leu Asn
225                 230                 235                 240

Asn Phe His Asn Leu Leu Arg Phe Trp Gln Gln His Tyr Leu His Lys
                 245                 250                 255

Asp Lys Asp Ser Thr Cys Leu Glu Asn Ser Ser Cys Ile Ser Phe Ser
             260                 265                 270

Tyr Trp Lys Glu Thr Val Ser Ile Leu Leu Asn Pro Asp Arg Gln Ser
         275                 280                 285

Pro Ser Ala Leu Val Ser Tyr Ile Glu Glu Pro Tyr Met Asp Ile Asp
290                 295                 300

Arg Asp Phe Thr Glu Glu
305                 310

(2) INFORMATION FOR SEQ ID NO:11:

(i) SEQUENCE CHARACTERISTICS:
        (A) LENGTH: 2735 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 2..1822

(xi) SEQUENCE DESCRIPTION: SEQ ID NO:11:

G GAG ATC AGT CGG AAG GTG TAC AAG GGA ATG TTA GAC CTC CTC AAG        46
  Glu Ile Ser Arg Lys Val Tyr Lys Gly Met Leu Asp Leu Leu Lys
   1               5                  10                  15

TGT ACA GTC CTC AGC TTG GAG CAG TCC TAT GCC CAC GCG GGT CTG GGT     94
Cys Thr Val Leu Ser Leu Glu Gln Ser Tyr Ala His Ala Gly Leu Gly
             20                  25                  30

GGC ATG GCC AGC ATC TTT GGG CTT TTG GAG ATT GCC CAG ACC CAC TAC    142
```

```
Gly Met Ala Ser Ile Phe Gly Leu Leu Glu Ile Ala Gln Thr His Tyr
             35                  40                  45

TAT AGT AAA GAA CCA GAC AAG CGG AAG AGA AGT CCA ACA GAA AGT GTA       190
Tyr Ser Lys Glu Pro Asp Lys Arg Lys Arg Ser Pro Thr Glu Ser Val
         50                  55                  60

AAT ACC CCA GTT GGC AAG GAT CCT GGC CTA GCT GGG CGG GGG GAC CCA       238
Asn Thr Pro Val Gly Lys Asp Pro Gly Leu Ala Gly Arg Gly Asp Pro
     65                  70                  75

AAG GCT ATG GCA CAA CTG AGA GTT CCA CAA CTG GGA CCT CGG GCA CCA       286
Lys Ala Met Ala Gln Leu Arg Val Pro Gln Leu Gly Pro Arg Ala Pro
 80                  85                  90                  95

AGT GCC ACA GGA AAG GGT CCT AAG GAA CTG GAC ACC AGA AGT TTA AAG       334
Ser Ala Thr Gly Lys Gly Pro Lys Glu Leu Asp Thr Arg Ser Leu Lys
                100                 105                 110

GAA GAA AAT TTT ATA GCA TCT ATT GGG CCT GAA GTA ATC AAA CCT GTC       382
Glu Glu Asn Phe Ile Ala Ser Ile Gly Pro Glu Val Ile Lys Pro Val
             115                 120                 125

TTT GAC CTT GGT GAG ACA GAG GAG AAA AAG TCC CAG ATC AGC GCA GAC       430
Phe Asp Leu Gly Glu Thr Glu Glu Lys Lys Ser Gln Ile Ser Ala Asp
         130                 135                 140

AGT GGT GTG AGC CTG ACG TCT AGT TCC CAG AGG ACT GAT CAA GAC TCT       478
Ser Gly Val Ser Leu Thr Ser Ser Ser Gln Arg Thr Asp Gln Asp Ser
145                 150                 155

GTC ATC GGC GTG AGT CCA GCT GTT ATG ATC CGC AGC TCA AGT CAG GAT       526
Val Ile Gly Val Ser Pro Ala Val Met Ile Arg Ser Ser Ser Gln Asp
160                 165                 170                 175

TCT GAA GTT AGC ACC GTG GTG AGT AAT AGC TCT GGA GAG ACC CTT GGA       574
Ser Glu Val Ser Thr Val Val Ser Asn Ser Ser Gly Glu Thr Leu Gly
                180                 185                 190

GCT GAC AGT GAC TTG AGC AGC AAT GCA GGT GAT GGA CCA GGT GGC GAG       622
Ala Asp Ser Asp Leu Ser Ser Asn Ala Gly Asp Gly Pro Gly Gly Glu
             195                 200                 205

GGC AGT GTT CAC CTG GCA AGC TCT CGG GGC ACT TTG TCT GAT AGT GAA       670
Gly Ser Val His Leu Ala Ser Ser Arg Gly Thr Leu Ser Asp Ser Glu
         210                 215                 220

ATT GAG ACC AAC TCT GCC ACA AGC ACC ATC TTT GGT AAA GCC CAC AGC       718
Ile Glu Thr Asn Ser Ala Thr Ser Thr Ile Phe Gly Lys Ala His Ser
225                 230                 235

TTG AAG CCA AGC ATA AAG GAG AAG CTG GCA GGC AGC CCC ATT CGT ACT       766
Leu Lys Pro Ser Ile Lys Glu Lys Leu Ala Gly Ser Pro Ile Arg Thr
240                 245                 250                 255

TCT GAA GAT GTG AGC CAG CGA GTC TAT CTC TAT GAG GGA CTC CTA GGC       814
Ser Glu Asp Val Ser Gln Arg Val Tyr Leu Tyr Glu Gly Leu Leu Gly
                260                 265                 270

AAA GAG CGT TCT ACT TTA TGG GAC CAA ATG CAA TTC TGG GAA GAT GCC       862
Lys Glu Arg Ser Thr Leu Trp Asp Gln Met Gln Phe Trp Glu Asp Ala
             275                 280                 285

TTC TTA GAT GCT GTG ATG TTG GAG AGA GAA GGG ATG GGT ATG GAC CAG       910
Phe Leu Asp Ala Val Met Leu Glu Arg Glu Gly Met Gly Met Asp Gln
         290                 295                 300

GGT CCC CAG GAA ATG ATC GAC AGG TAC CTG TCC CTT GGA GAA CAT GAC       958
Gly Pro Gln Glu Met Ile Asp Arg Tyr Leu Ser Leu Gly Glu His Asp
305                 310                 315

CGG AAG CGC CTG GAA GAT GAT GAA GAT CGC TTG CTG GCC ACA CTT CTG      1006
Arg Lys Arg Leu Glu Asp Asp Glu Asp Arg Leu Leu Ala Thr Leu Leu
320                 325                 330                 335

CAC AAC CTC ATC TCC TAC ATG CTG CTG ATG AAG GTA AAT AAG AAT GAC      1054
His Asn Leu Ile Ser Tyr Met Leu Leu Met Lys Val Asn Lys Asn Asp
                340                 345                 350

ATC CGC AAG AAG GTG AGG CGC CTA ATG GGA AAG TCG CAC ATT GGG CTT      1102
```

```
Ile Arg Lys Lys Val Arg Arg Leu Met Gly Lys Ser His Ile Gly Leu
            355                 360                 365
GTG TAC AGC CAG CAA ATC AAT GAG GTG CTT GAT CAG CTG GCG AAC CTG         1150
Val Tyr Ser Gln Gln Ile Asn Glu Val Leu Asp Gln Leu Ala Asn Leu
            370                 375                 380
AAT GGA CGC GAT CTC TCT ATC TGG TCC AGT GGC AGC CGG CAC ATG AAG         1198
Asn Gly Arg Asp Leu Ser Ile Trp Ser Ser Gly Ser Arg His Met Lys
            385                 390                 395
AAG CAG ACA TTT GTG GTA CAT GCA GGG ACA GAT ACA AAC GGA GAT ATC         1246
Lys Gln Thr Phe Val Val His Ala Gly Thr Asp Thr Asn Gly Asp Ile
400                 405                 410                 415
TTT TTC ATG GAG GTG TGC GAT GAC TGT GTG GTG TTG CGT AGT AAC ATC         1294
Phe Phe Met Glu Val Cys Asp Asp Cys Val Val Leu Arg Ser Asn Ile
            420                 425                 430
GGA ACA GTG TAT GAG CGC TGG TGG TAC GAG AAG CTC ATC AAC ATG ACC         1342
Gly Thr Val Tyr Glu Arg Trp Trp Tyr Glu Lys Leu Ile Asn Met Thr
            435                 440                 445
TAC TGT CCC AAG ACG AAG GTG TTG TGC TTG TGG CGT AGA AAT GGC TCT         1390
Tyr Cys Pro Lys Thr Lys Val Leu Cys Leu Trp Arg Arg Asn Gly Ser
            450                 455                 460
GAG ACC CAG CTC AAC AAG TTC TAT ACT AAA AAG TGT CGG GAG CTG TAC         1438
Glu Thr Gln Leu Asn Lys Phe Tyr Thr Lys Lys Cys Arg Glu Leu Tyr
            465                 470                 475
TAC TGT GTG AAG GAC AGC ATG GAG CGC GCT GCC GCC CGA CAG CAA AGC         1486
Tyr Cys Val Lys Asp Ser Met Glu Arg Ala Ala Ala Arg Gln Gln Ser
480                 485                 490                 495
ATC AAA CCC GGA CCT GAA TTG GGT GGC GAG TTC CCT GTG CAG GAC CTG         1534
Ile Lys Pro Gly Pro Glu Leu Gly Gly Glu Phe Pro Val Gln Asp Leu
            500                 505                 510
AAG ACT GGT GAG GGT GGC CTG CTG CAG GTG ACC CTG GAA GGG ATC AAC         1582
Lys Thr Gly Glu Gly Gly Leu Leu Gln Val Thr Leu Glu Gly Ile Asn
            515                 520                 525
CTC AAA TTC ATG CAC AAT CAG GTT TTC ATA GAG CTG AAT CAC ATT AAA         1630
Leu Lys Phe Met His Asn Gln Val Phe Ile Glu Leu Asn His Ile Lys
            530                 535                 540
AAG TGC AAT ACA GTT CGA GGC GTC TTT GTC CTG GAG GAA TTT GTT CCT         1678
Lys Cys Asn Thr Val Arg Gly Val Phe Val Leu Glu Glu Phe Val Pro
545                 550                 555
GAA ATT AAA GAA GTG GTG AGC CAC AAG TAC AAG ACA CCA ATG GCC CAC         1726
Glu Ile Lys Glu Val Val Ser His Lys Tyr Lys Thr Pro Met Ala His
560                 565                 570                 575
GAA ATC TGC TAC TCC GTA TTA TGT CTC TTC TCG TAC GTG GCT GCA GTT         1774
Glu Ile Cys Tyr Ser Val Leu Cys Leu Phe Ser Tyr Val Ala Ala Val
            580                 585                 590
CAT AGC AGT GAG GAA GAT CTC AGA ACC CCG CCC CGG CCT GTC TCT AGC         1822
His Ser Ser Glu Glu Asp Leu Arg Thr Pro Pro Arg Pro Val Ser Ser
            595                 600                 605
TGATGGAGAG GGGCTACGCA GCTGCCCCAG CCCAGGGCAC GCCCCTGGCC CCTTGCTGTT      1882
CCCAAGTGCA CGATGCTGCT GTGACTGAGG AGTGGATGAT GCTCGTGTGT CCTCTGCAAG      1942
CCCCCTGCTG TGGCTTGGTT GGTTACCGGT TATGTGTCCC TCTGAGTGTG TCTTGAGCGT      2002
GTCCACCTTC TCCCTCTCCA CTCCCAGAAG ACCAAACTGC CTTCCCCTCA GGGCTCAAGA      2062
ATGTGTACAG TCTGTGGGGC CGGTGTGAAC CCACTATTTT GTGTCCTTGA GACATTTGTG      2122
TTGTGGTTCC TTGTCCTTGT CCCTGGCGTT ATAACTGTCC ACTGCAAGAG TCTGGCTCTC      2182
CCTTCTCTGT GACCCGGCAT GACTGGGCGC TGGAGCAGTT TCACTCTGT GAGGAGTGAG       2242
GGAACCCTGG GGCTCACCCT CTCAGAGGAA GGGCACAGAG AGGAAGGGAA GAATTGGGGG     2302
GCAGCCGGAG TGAGTGGCAG CCTCCCTGCT TCCTTCTGCA TTCCCAAGCC GGCAGCTACT     2362
```

-continued

```
GCCCAGGGCC CGCAGTGTTG GCTGCTGCCT GCCACAGCCT CTGTGACTGC AGTGGAGCGG    2422

CGAATTCCCT GTGGCCTGCC ACGCCTTCGG CATCAGAGGA TGGAGTGGTC GAGGCTAGTG    2482

GAGTCCCAGG GACCGCTGGC TGCTCTGCCT GAGCATCAGG GAGGGGGCAG GAAAGACCAA    2542

GCTGGGTTTG CACATCTGTC TGCAGGCTGT CTCTCCAGGC ACGGGGTGTC AGGAGGGAGA    2602

GACAGCCTGG GTATGGGCAA GAAATGACTG TAAATATTTC AGCCCCACAT TATTTATAGA    2662

AAATGTACAG TTGTGTGAAT GTGAAATAAA TGTCCTCAAC TCCCAAAAAA AAAAAAAAA     2722

AAAAAAAAA AAA                                                         2735
```

(2) INFORMATION FOR SEQ ID NO:12:

(i) SEQUENCE CHARACTERISTICS:
        (A) LENGTH: 607 amino acids
        (B) TYPE: amino acid
        (D) TOPOLOGY: linear (ii) MOLECULE TYPE: protein (xi) SEQUENCE DESCRIPTION: SEQ ID NO:12:

```
Glu Ile Ser Arg Lys Val Tyr Lys Gly Met Leu Asp Leu Leu Lys Cys
 1               5                  10                  15

Thr Val Leu Ser Leu Glu Gln Ser Tyr Ala His Ala Gly Leu Gly Gly
            20                  25                  30

Met Ala Ser Ile Phe Gly Leu Leu Glu Ile Ala Gln Thr His Tyr Tyr
        35                  40                  45

Ser Lys Glu Pro Asp Lys Arg Lys Ser Pro Thr Glu Ser Val Asn
    50                  55                  60

Thr Pro Val Gly Lys Asp Pro Gly Leu Ala Gly Arg Gly Asp Pro Lys
65                  70                  75                  80

Ala Met Ala Gln Leu Arg Val Pro Gln Leu Gly Pro Arg Ala Pro Ser
            85                  90                  95

Ala Thr Gly Lys Gly Pro Lys Glu Leu Asp Thr Arg Ser Leu Lys Glu
        100                 105                 110

Glu Asn Phe Ile Ala Ser Ile Gly Pro Glu Val Ile Lys Pro Val Phe
    115                 120                 125

Asp Leu Gly Glu Thr Glu Glu Lys Lys Ser Gln Ile Ser Ala Asp Ser
130                 135                 140

Gly Val Ser Leu Thr Ser Ser Ser Gln Arg Thr Asp Gln Asp Ser Val
145                 150                 155                 160

Ile Gly Val Ser Pro Ala Val Met Ile Arg Ser Ser Ser Gln Asp Ser
            165                 170                 175

Glu Val Ser Thr Val Val Ser Asn Ser Ser Gly Glu Thr Leu Gly Ala
        180                 185                 190

Asp Ser Asp Leu Ser Ser Asn Ala Gly Asp Gly Pro Gly Gly Glu Gly
    195                 200                 205

Ser Val His Leu Ala Ser Ser Arg Gly Thr Leu Ser Asp Ser Glu Ile
    210                 215                 220

Glu Thr Asn Ser Ala Thr Ser Thr Ile Phe Gly Lys Ala His Ser Leu
225                 230                 235                 240

Lys Pro Ser Ile Lys Glu Lys Leu Ala Gly Ser Pro Ile Arg Thr Ser
            245                 250                 255

Glu Asp Val Ser Gln Arg Val Tyr Leu Tyr Glu Gly Leu Leu Gly Lys
        260                 265                 270

Glu Arg Ser Thr Leu Trp Asp Gln Met Gln Phe Trp Glu Asp Ala Phe
    275                 280                 285
```

```
Leu Asp Ala Val Met Leu Glu Arg Gly Met Gly Met Asp Gln Gly
    290                 295                 300

Pro Gln Glu Met Ile Asp Arg Tyr Leu Ser Leu Gly Glu His Asp Arg
305                 310                 315                 320

Lys Arg Leu Glu Asp Asp Glu Asp Arg Leu Leu Ala Thr Leu Leu His
                325                 330                 335

Asn Leu Ile Ser Tyr Met Leu Met Lys Val Asn Lys Asn Asp Ile
            340                 345                 350

Arg Lys Lys Val Arg Arg Leu Met Gly Lys Ser His Ile Gly Leu Val
        355                 360                 365

Tyr Ser Gln Gln Ile Asn Glu Val Leu Asp Gln Leu Ala Asn Leu Asn
    370                 375                 380

Gly Arg Asp Leu Ser Ile Trp Ser Ser Gly Ser Arg His Met Lys Lys
385                 390                 395                 400

Gln Thr Phe Val Val His Ala Gly Thr Asp Thr Asn Gly Asp Ile Phe
                405                 410                 415

Phe Met Glu Val Cys Asp Asp Cys Val Val Leu Arg Ser Asn Ile Gly
            420                 425                 430

Thr Val Tyr Glu Arg Trp Trp Tyr Glu Lys Leu Ile Asn Met Thr Tyr
        435                 440                 445

Cys Pro Lys Thr Lys Val Leu Cys Leu Trp Arg Arg Asn Gly Ser Glu
    450                 455                 460

Thr Gln Leu Asn Lys Phe Tyr Thr Lys Lys Cys Arg Glu Leu Tyr Tyr
465                 470                 475                 480

Cys Val Lys Asp Ser Met Glu Arg Ala Ala Arg Gln Gln Ser Ile
                485                 490                 495

Lys Pro Gly Pro Glu Leu Gly Gly Glu Phe Pro Val Gln Asp Leu Lys
            500                 505                 510

Thr Gly Glu Gly Gly Leu Leu Gln Val Thr Leu Glu Gly Ile Asn Leu
        515                 520                 525

Lys Phe Met His Asn Gln Val Phe Ile Glu Leu Asn His Ile Lys Lys
    530                 535                 540

Cys Asn Thr Val Arg Gly Val Phe Val Leu Glu Glu Phe Val Pro Glu
545                 550                 555                 560

Ile Lys Glu Val Val Ser His Lys Tyr Lys Thr Pro Met Ala His Glu
                565                 570                 575

Ile Cys Tyr Ser Val Leu Cys Leu Phe Ser Tyr Val Ala Ala Val His
            580                 585                 590

Ser Ser Glu Glu Asp Leu Arg Thr Pro Pro Arg Pro Val Ser Ser
        595                 600                 605

(2) INFORMATION FOR SEQ ID NO:13:

(i) SEQUENCE CHARACTERISTICS:
        (A) LENGTH: 3225 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 3..2846

(xi) SEQUENCE DESCRIPTION: SEQ ID NO:13:
```

| | |
|---|---|
| CC CAG ACT CGC CCC GCC CCA GAG ACT GCG CCT GCG CGG GCA CGA GAC<br>   Gln Thr Arg Pro Ala Pro Glu Thr Ala Pro Ala Arg Ala Arg Asp<br>    1               5                  10               15 | 47 |
| ACC CTC TCC GCG ATG ACT GCC AGC TCA GTG GAG CAG CTG CGG AAG GAG<br>Thr Leu Ser Ala Met Thr Ala Ser Ser Val Glu Gln Leu Arg Lys Glu<br>               20                  25               30 | 95 |
| GGC AAT GAG CTG TTC AAA TGT GGA GAC TAC GGG GGC GCC CTG GCG GCC<br>Gly Asn Glu Leu Phe Lys Cys Gly Asp Tyr Gly Gly Ala Leu Ala Ala<br>               35                  40               45 | 143 |
| TAC ACT CAG GCC CTG GGT CTG GAC GCG ACG CCC CAG GAC CAG GCC GTT<br>Tyr Thr Gln Ala Leu Gly Leu Asp Ala Thr Pro Gln Asp Gln Ala Val<br>         50                  55               60 | 191 |
| CTG CAC CGG AAC CGG GCC GCC TGC CAC CTC AAG CTG GAA GAT TAC GAC<br>Leu His Arg Asn Arg Ala Ala Cys His Leu Lys Leu Glu Asp Tyr Asp<br>         65                  70               75 | 239 |
| AAA GCA GAA ACA GAG GCA TCC AAA GCC ATT GAA AAG GAT GGT GGG GAT<br>Lys Ala Glu Thr Glu Ala Ser Lys Ala Ile Glu Lys Asp Gly Gly Asp<br> 80                85                 90               95 | 287 |
| GTC AAA GCA CTC TAC CGG CGG AGC CAA GCC CTA GAG AAG CTG GGC CGC<br>Val Lys Ala Leu Tyr Arg Arg Ser Gln Ala Leu Glu Lys Leu Gly Arg<br>              100              105             110 | 335 |
| CTG GAC CAG GCT GTC CTT GAC CTG CAG AGA TGT GTG AGC TTG GAG CCC<br>Leu Asp Gln Ala Val Leu Asp Leu Gln Arg Cys Val Ser Leu Glu Pro<br>              115              120             125 | 383 |
| AAG AAC AAA GTT TTC CAG GAG GCC TTG CGG AAC ATC GGG GGC CAG ATT<br>Lys Asn Lys Val Phe Gln Glu Ala Leu Arg Asn Ile Gly Gly Gln Ile<br>         130                 135             140 | 431 |
| CAG GAG AAG GTG CGA TAC ATG TCC TCG ACG GAT GCC AAA GTG GAA CAG<br>Gln Glu Lys Val Arg Tyr Met Ser Ser Thr Asp Ala Lys Val Glu Gln<br>         145                 150             155 | 479 |
| ATG TTT CAG ATA CTG TTG GAC CCA GAA GAG AAG GGC ACT GAG AAA AAG<br>Met Phe Gln Ile Leu Leu Asp Pro Glu Glu Lys Gly Thr Glu Lys Lys<br>160                 165                 170             175 | 527 |
| CAA AAG GCT TCT CAG AAC CTG GTG GTG CTG GCC AGG GAG GAT GCT GGA<br>Gln Lys Ala Ser Gln Asn Leu Val Val Leu Ala Arg Glu Asp Ala Gly<br>              180              185             190 | 575 |
| GCG GAG AAG ATC TTC CGG AGT AAT GGG GTT CAG CTC TTG CAA CGT TTA<br>Ala Glu Lys Ile Phe Arg Ser Asn Gly Val Gln Leu Leu Gln Arg Leu<br>         195                 200             205 | 623 |
| CTG GAC ATG GGA GAG ACT GAC CTC ATG CTG GCG GCT CTG CGT ACG CTG<br>Leu Asp Met Gly Glu Thr Asp Leu Met Leu Ala Ala Leu Arg Thr Leu<br>         210                 215             220 | 671 |
| GTT GGC ATT TGC TCT GAG CAT CAG TCA CGG ACA GTG GCA ACC CTG AGC<br>Val Gly Ile Cys Ser Glu His Gln Ser Arg Thr Val Ala Thr Leu Ser<br>         225                 230             235 | 719 |
| ATA CTG GGA ACT CGG CGA GTA GTC TCC ATC CTG GGC GTG GAA AGC CAG<br>Ile Leu Gly Thr Arg Arg Val Val Ser Ile Leu Gly Val Glu Ser Gln<br>240                 245                 250             255 | 767 |
| GCT GTG TCC CTG GCT GCC TGC CAC CTG CTG CAG GTT ATG TTT GAT GCC<br>Ala Val Ser Leu Ala Ala Cys His Leu Leu Gln Val Met Phe Asp Ala<br>              260              265             270 | 815 |
| CTC AAG GAA GGT GTC AAA AAA GGC TTC CGA GGC AAA GAA GGT GCC ATC<br>Leu Lys Glu Gly Val Lys Lys Gly Phe Arg Gly Lys Glu Gly Ala Ile<br>         275                 280             285 | 863 |
| ATT GTG GAT CCT GCC CGG GAG CTG AAG GTC CTC ATC AGT AAC CTC TTA<br>Ile Val Asp Pro Ala Arg Glu Leu Lys Val Leu Ile Ser Asn Leu Leu<br>         290                 295             300 | 911 |
| GAT CTG CTG ACA GAG GTG GGG GTC TCT GGC CAA GGC CGA GAC AAT GCC<br>Asp Leu Leu Thr Glu Val Gly Val Ser Gly Gln Gly Arg Asp Asn Ala<br>         305                 310             315 | 959 |

```
CTG ACC CTC CTG ATT AAA GCG GTG CCC CGG AAG TCT CTC AAG GAC CCC        1007
Leu Thr Leu Leu Ile Lys Ala Val Pro Arg Lys Ser Leu Lys Asp Pro
320                 325                 330                 335

AAC AAC AGC CTC ACC CTC TGG GTC ATC GAC CAA GGT CTG AAA AAG ATT        1055
Asn Asn Ser Leu Thr Leu Trp Val Ile Asp Gln Gly Leu Lys Lys Ile
            340                 345                 350

TTG GAA GTG GGG GGC TCT CTA CAG GAC CCT CCT GGG GAG CTC GCA GTG        1103
Leu Glu Val Gly Gly Ser Leu Gln Asp Pro Pro Gly Glu Leu Ala Val
                355                 360                 365

ACC GCA AAC AGC CGC ATG AGC GCC TCT ATT CTC CTC AGC AAG CTC TTT        1151
Thr Ala Asn Ser Arg Met Ser Ala Ser Ile Leu Leu Ser Lys Leu Phe
    370                 375                 380

GAT GAC CTC AAG TGT GAT GCG GAG AGG GAG AAT TTC CAC AGA CTT TGT        1199
Asp Asp Leu Lys Cys Asp Ala Glu Arg Glu Asn Phe His Arg Leu Cys
385                 390                 395

GAA AAC TAC ATC AAG AGC TGG TTT GAG GGC CAA GGG CTG GCC GGG AAG        1247
Glu Asn Tyr Ile Lys Ser Trp Phe Glu Gly Gln Gly Leu Ala Gly Lys
400                 405                 410                 415

CTA CGG GCC ATC CAG ACG GTG TCC TGC CTC CTG CAG GGC CCA TGT GAC        1295
Leu Arg Ala Ile Gln Thr Val Ser Cys Leu Leu Gln Gly Pro Cys Asp
                420                 425                 430

GCT GGC AAC CGG GCC TTG GAG CTG AGC GGT GTC ATG GAG AGT GTG ATT        1343
Ala Gly Asn Arg Ala Leu Glu Leu Ser Gly Val Met Glu Ser Val Ile
        435                 440                 445

GCT CTG TGT GCC TCT GAG CAG GAG GAG GAG CAG CTG GTG GCC GTG GAG        1391
Ala Leu Cys Ala Ser Glu Gln Glu Glu Glu Gln Leu Val Ala Val Glu
        450                 455                 460

GCT CTG ATC CAT GCA GCC GGC AAG GCT AAG CGG GCC TCA TTC ATC ACT        1439
Ala Leu Ile His Ala Ala Gly Lys Ala Lys Arg Ala Ser Phe Ile Thr
465                 470                 475

GCC AAT GGT GTC TCG CTG CTG AAG GAC CTA TAT AAG TGC AGC GAG AAG        1487
Ala Asn Gly Val Ser Leu Leu Lys Asp Leu Tyr Lys Cys Ser Glu Lys
480                 485                 490                 495

GAC AGC ATC CGC ATC CGG GCG CTA GTG GGA CTC TGT AAG CTC GGT TCG        1535
Asp Ser Ile Arg Ile Arg Ala Leu Val Gly Leu Cys Lys Leu Gly Ser
                500                 505                 510

GCT GGA GGG ACT GAC TTC AGC ATG AAG CAG TTT GCT GAA GGC TCC ACT        1583
Ala Gly Gly Thr Asp Phe Ser Met Lys Gln Phe Ala Glu Gly Ser Thr
            515                 520                 525

CTC AAA CTG GCT AAG CAG TGT CGA AAG TGG CTG TGC AAT GAC CAG ATC        1631
Leu Lys Leu Ala Lys Gln Cys Arg Lys Trp Leu Cys Asn Asp Gln Ile
        530                 535                 540

GAC GCA GGC ACT CGG CGC TGG GCA GTG GAG GGC CTG GCT TAC CTG ACC        1679
Asp Ala Gly Thr Arg Arg Trp Ala Val Glu Gly Leu Ala Tyr Leu Thr
        545                 550                 555

TTT GAT GCC GAC GTG AAG GAA GAG TTT GTG GAG GAT GCG GCT GCT CTG        1727
Phe Asp Ala Asp Val Lys Glu Glu Phe Val Glu Asp Ala Ala Ala Leu
560                 565                 570                 575

AAA GCT CTG TTC CAG CTC AGC AGG TTG GAG GAG AGG TCA GTG CTC TTT        1775
Lys Ala Leu Phe Gln Leu Ser Arg Leu Glu Glu Arg Ser Val Leu Phe
                580                 585                 590

GCG GTG GCC TCA GCG CTG GTG AAC TGC ACC AAC AGC TAT GAC TAC GAG        1823
Ala Val Ala Ser Ala Leu Val Asn Cys Thr Asn Ser Tyr Asp Tyr Glu
            595                 600                 605

GAG CCC GAC CCC AAG ATG GTG GAG CTG GCC AAG TAT GCC AAG CAG CAT        1871
Glu Pro Asp Pro Lys Met Val Glu Leu Ala Lys Tyr Ala Lys Gln His
        610                 615                 620

GTG CCC GAG CAG CAC CCC AAG GAC AAG CCA AGC TTC GTG CGG GCT CGG        1919
Val Pro Glu Gln His Pro Lys Asp Lys Pro Ser Phe Val Arg Ala Arg
625                 630                 635
```

| | | |
|---|---|---|
| GTG AAG AAG CTG CTG GCA GCG GGT GTG GTG TCG GCC ATG GTG TGC ATG<br>Val Lys Lys Leu Leu Ala Ala Gly Val Val Ser Ala Met Val Cys Met<br>640                          645                      650                     655 | | 1967 |
| GTG AAG ACG GAG AGC CCT GTG CTG ACC AGT TCC TGC AGA GAG CTG CTC<br>Val Lys Thr Glu Ser Pro Val Leu Thr Ser Ser Cys Arg Glu Leu Leu<br>                        660                      665                     670 | | 2015 |
| TCC AGG GTC TTC TTG GCT TTA GTG GAA GAG GTA GAG GAC CGA GGC ACT<br>Ser Arg Val Phe Leu Ala Leu Val Glu Glu Val Glu Asp Arg Gly Thr<br>            675                      680                     685 | | 2063 |
| GTG GTT GCC CAG GGA GGC GGC AGG GCG CTG ATC CCG CTG GCC CTG GAA<br>Val Val Ala Gln Gly Gly Gly Arg Ala Leu Ile Pro Leu Ala Leu Glu<br>                        690                      695                     700 | | 2111 |
| GGC ACG GAC GTG GGG CAG ACA AAG GCA GCC CAG GCC CTT GCC AAG CTC<br>Gly Thr Asp Val Gly Gln Thr Lys Ala Ala Gln Ala Leu Ala Lys Leu<br>     705                      710                      715 | | 2159 |
| ACC ATC ACC TCC AAC CCG GAG ATG ACC TTC CCT GGC GAG CGG ATC TAT<br>Thr Ile Thr Ser Asn Pro Glu Met Thr Phe Pro Gly Glu Arg Ile Tyr<br>720                          725                      730                     735 | | 2207 |
| GAG GTG GTC CGG CCC CTC GTC TCC CTG TTG CAC CTC AAC TGC TCA GGC<br>Glu Val Val Arg Pro Leu Val Ser Leu Leu His Leu Asn Cys Ser Gly<br>                 740                      745                     750 | | 2255 |
| CTG CAG AAC TTC GAG GCG CTC ATG GCC CTA ACA AAC CTG GCT GGG ATC<br>Leu Gln Asn Phe Glu Ala Leu Met Ala Leu Thr Asn Leu Ala Gly Ile<br>            755                      760                     765 | | 2303 |
| AGC GAG AGG CTC CGG CAG AAG ATC CTG AAG GAG AAG GCT GTG CCC ATG<br>Ser Glu Arg Leu Arg Gln Lys Ile Leu Lys Glu Lys Ala Val Pro Met<br>     770                      775                      780 | | 2351 |
| ATA GAA GGC TAC ATG TTT GAG GAG CAT GAG ATG ATC CGC CGG GCA GCC<br>Ile Glu Gly Tyr Met Phe Glu Glu His Glu Met Ile Arg Arg Ala Ala<br>785                          790                      795 | | 2399 |
| ACG GAG TGC ATG TGT AAC TTG GCC ATG AGC AAG GAG GTG CAG GAC CTC<br>Thr Glu Cys Met Cys Asn Leu Ala Met Ser Lys Glu Val Gln Asp Leu<br>800                          805                      810                     815 | | 2447 |
| TTC GAA GCC CAG GGC AAT GAC CGA CTG AAG CTG CTG GTG CTG TAC AGT<br>Phe Glu Ala Gln Gly Asn Asp Arg Leu Lys Leu Leu Val Leu Tyr Ser<br>                 820                      825                     830 | | 2495 |
| GGA GAG GAT GAT GAG CTG CTA CAG CGG GCA GCT GCC GGG GGC TTG GCC<br>Gly Glu Asp Asp Glu Leu Leu Gln Arg Ala Ala Ala Gly Gly Leu Ala<br>                 835                      840                     845 | | 2543 |
| ATG CTT ACC TCC ATG CGG CCC ACG CTC TGC AGC CGC ATT CCC CAA GTG<br>Met Leu Thr Ser Met Arg Pro Thr Leu Cys Ser Arg Ile Pro Gln Val<br>     850                      855                      860 | | 2591 |
| ACC ACA CAC TGG CTG GAG ATC CTG CAG GCC CTG CTT CTG AGC TCC AAC<br>Thr Thr His Trp Leu Glu Ile Leu Gln Ala Leu Leu Leu Ser Ser Asn<br>865                          870                      875 | | 2639 |
| CAG GAG CTG CAG CAC CGG GGT GCT GTG GTG GTG CTG AAC ATG GTG GAG<br>Gln Glu Leu Gln His Arg Gly Ala Val Val Val Leu Asn Met Val Glu<br>880                          885                      890                     895 | | 2687 |
| GCC TCG AGG GAG ATT GCC AGC ACC CTG ATG GAG AGT GAG ATG ATG GAG<br>Ala Ser Arg Glu Ile Ala Ser Thr Leu Met Glu Ser Glu Met Met Glu<br>                 900                      905                     910 | | 2735 |
| ATC TTG TCA GTG CTA GCT AAG GGT GAC CAC AGC CCT GTC ACA AGG GCT<br>Ile Leu Ser Val Leu Ala Lys Gly Asp His Ser Pro Val Thr Arg Ala<br>               915                      920                     925 | | 2783 |
| GCT GCA GCC TGC CTG GAC AAA GCA GTG GAA TAT GGG CTT ATC CAA CCC<br>Ala Ala Ala Cys Leu Asp Lys Ala Val Glu Tyr Gly Leu Ile Gln Pro<br>             930                      935                     940 | | 2831 |
| AAC CAA GAT GGA GAG TGAGGGGGTT GTCCCTGGGC CCAAGGCTCA TGCACACGCT<br>Asn Gln Asp Gly Glu<br>     945 | | 2886 |

```
ACCTATTGTG GCACGGAGAG TAAGGACGGA AGCAGCTTTG GCTGGTGGTG GCTGGCATGC    2946

CCAATACTCT TGCCCATCCT CGCTTGCTGC CCTAGGATGT CCTCTGTTCT GAGTCAGCGG    3006

CCACGTTCAG TCACACAGCC CTGCTTGGCC AGCACTGCCT GCAGCCTCAC TCAGAGGGGC    3066

CCTTTTTCTG TACTACTGTA GTCAGCTGGG AATGGGGAAG GTGCATCCCA ACACAGCCTG    3126

TGGATCCTGG GGCATTTGGA AGGGCGCACA CATCAGCAGC CTCACCAGCT GTGAGCCTGC    3186

TATCAGGCCT GCCCCTCCAA TAAAAGTGTG TAGAACTCC                           3225
```

(2) INFORMATION FOR SEQ ID NO:14:

(i) SEQUENCE CHARACTERISTICS:
        (A) LENGTH: 948 amino acids
        (B) TYPE: amino acid
        (D) TOPOLOGY: linear (ii) MOLECULE TYPE: protein (xi) SEQUENCE DESCRIPTION: SEQ ID NO:14:

```
Gln Thr Arg Pro Ala Pro Glu Thr Ala Pro Ala Arg Ala Arg Asp Thr
  1               5                  10                  15

Leu Ser Ala Met Thr Ala Ser Ser Val Glu Gln Leu Arg Lys Glu Gly
             20                  25                  30

Asn Glu Leu Phe Lys Cys Gly Asp Tyr Gly Gly Ala Leu Ala Ala Tyr
         35                  40                  45

Thr Gln Ala Leu Gly Leu Asp Ala Thr Pro Gln Asp Gln Ala Val Leu
     50                  55                  60

His Arg Asn Arg Ala Ala Cys His Leu Lys Leu Glu Asp Tyr Asp Lys
 65                  70                  75                  80

Ala Glu Thr Glu Ala Ser Lys Ala Ile Glu Lys Asp Gly Gly Asp Val
                 85                  90                  95

Lys Ala Leu Tyr Arg Arg Ser Gln Ala Leu Glu Lys Leu Gly Arg Leu
            100                 105                 110

Asp Gln Ala Val Leu Asp Leu Gln Arg Cys Val Ser Leu Glu Pro Lys
        115                 120                 125

Asn Lys Val Phe Gln Glu Ala Leu Arg Asn Ile Gly Gly Gln Ile Gln
    130                 135                 140

Glu Lys Val Arg Tyr Met Ser Ser Thr Asp Ala Lys Val Glu Gln Met
145                 150                 155                 160

Phe Gln Ile Leu Leu Asp Pro Glu Glu Lys Gly Thr Glu Lys Lys Gln
                165                 170                 175

Lys Ala Ser Gln Asn Leu Val Val Leu Ala Arg Glu Asp Ala Gly Ala
            180                 185                 190

Glu Lys Ile Phe Arg Ser Asn Gly Val Gln Leu Leu Gln Arg Leu Leu
        195                 200                 205

Asp Met Gly Glu Thr Asp Leu Met Leu Ala Ala Leu Arg Thr Leu Val
    210                 215                 220

Gly Ile Cys Ser Glu His Gln Ser Arg Thr Val Ala Thr Leu Ser Ile
225                 230                 235                 240

Leu Gly Thr Arg Arg Val Val Ser Ile Leu Gly Val Glu Ser Gln Ala
                245                 250                 255

Val Ser Leu Ala Ala Cys His Leu Leu Gln Val Met Phe Asp Ala Leu
            260                 265                 270

Lys Glu Gly Val Lys Lys Gly Phe Arg Gly Lys Glu Gly Ala Ile Ile
        275                 280                 285

Val Asp Pro Ala Arg Glu Leu Lys Val Leu Ile Ser Asn Leu Leu Asp
    290                 295                 300
```

-continued

Leu Leu Thr Glu Val Gly Val Ser Gly Gln Gly Arg Asp Asn Ala Leu
305                 310                 315                 320

Thr Leu Leu Ile Lys Ala Val Pro Arg Lys Ser Leu Lys Asp Pro Asn
            325                 330                 335

Asn Ser Leu Thr Leu Trp Val Ile Asp Gln Gly Leu Lys Lys Ile Leu
            340                 345                 350

Glu Val Gly Gly Ser Leu Gln Asp Pro Pro Gly Glu Leu Ala Val Thr
        355                 360                 365

Ala Asn Ser Arg Met Ser Ala Ser Ile Leu Leu Ser Lys Leu Phe Asp
370                 375                 380

Asp Leu Lys Cys Asp Ala Glu Arg Glu Asn Phe His Arg Leu Cys Glu
385                 390                 395                 400

Asn Tyr Ile Lys Ser Trp Phe Glu Gly Gln Gly Leu Ala Gly Lys Leu
            405                 410                 415

Arg Ala Ile Gln Thr Val Ser Cys Leu Leu Gln Gly Pro Cys Asp Ala
            420                 425                 430

Gly Asn Arg Ala Leu Glu Leu Ser Gly Val Met Glu Ser Val Ile Ala
        435                 440                 445

Leu Cys Ala Ser Glu Gln Glu Glu Gln Leu Val Ala Val Glu Ala
450                 455                 460

Leu Ile His Ala Ala Gly Lys Ala Lys Arg Ala Ser Phe Ile Thr Ala
465                 470                 475                 480

Asn Gly Val Ser Leu Leu Lys Asp Leu Tyr Lys Cys Ser Glu Lys Asp
            485                 490                 495

Ser Ile Arg Ile Arg Ala Leu Val Gly Leu Cys Lys Leu Gly Ser Ala
            500                 505                 510

Gly Gly Thr Asp Phe Ser Met Lys Gln Phe Ala Glu Gly Ser Thr Leu
        515                 520                 525

Lys Leu Ala Lys Gln Cys Arg Lys Trp Leu Cys Asn Asp Gln Ile Asp
530                 535                 540

Ala Gly Thr Arg Arg Trp Ala Val Glu Gly Leu Ala Tyr Leu Thr Phe
545                 550                 555                 560

Asp Ala Asp Val Lys Glu Glu Phe Val Glu Asp Ala Ala Leu Lys
            565                 570                 575

Ala Leu Phe Gln Leu Ser Arg Leu Glu Glu Arg Ser Val Leu Phe Ala
            580                 585                 590

Val Ala Ser Ala Leu Val Asn Cys Thr Asn Ser Tyr Asp Tyr Glu Glu
        595                 600                 605

Pro Asp Pro Lys Met Val Glu Leu Ala Lys Tyr Ala Lys Gln His Val
610                 615                 620

Pro Glu Gln His Pro Lys Asp Lys Pro Ser Phe Val Arg Ala Arg Val
625                 630                 635                 640

Lys Lys Leu Leu Ala Ala Gly Val Val Ser Ala Met Val Cys Met Val
            645                 650                 655

Lys Thr Glu Ser Pro Val Leu Thr Ser Ser Cys Arg Glu Leu Leu Ser
            660                 665                 670

Arg Val Phe Leu Ala Leu Val Glu Glu Val Glu Asp Arg Gly Thr Val
        675                 680                 685

Val Ala Gln Gly Gly Gly Arg Ala Leu Ile Pro Leu Ala Leu Glu Gly
        690                 695                 700

Thr Asp Val Gly Gln Thr Lys Ala Ala Gln Ala Leu Ala Lys Leu Thr
705                 710                 715                 720

Ile Thr Ser Asn Pro Glu Met Thr Phe Pro Gly Glu Arg Ile Tyr Glu

```
                        725                 730                 735
Val Val Arg Pro Leu Val Ser Leu Leu His Leu Asn Cys Ser Gly Leu
            740                 745                 750

Gln Asn Phe Glu Ala Leu Met Ala Leu Thr Asn Leu Ala Gly Ile Ser
        755                 760                 765

Glu Arg Leu Arg Gln Lys Ile Leu Lys Glu Lys Ala Val Pro Met Ile
    770                 775                 780

Glu Gly Tyr Met Phe Glu Gln His Glu Met Ile Arg Arg Ala Ala Thr
785                 790                 795                 800

Glu Cys Met Cys Asn Leu Ala Met Ser Lys Glu Val Gln Asp Leu Phe
            805                 810                 815

Glu Ala Gln Gly Asn Asp Arg Leu Lys Leu Leu Val Leu Tyr Ser Gly
        820                 825                 830

Glu Asp Asp Glu Leu Leu Gln Arg Ala Ala Ala Gly Gly Leu Ala Met
            835                 840                 845

Leu Thr Ser Met Arg Pro Thr Leu Cys Ser Arg Ile Pro Gln Val Thr
    850                 855                 860

Thr His Trp Leu Glu Ile Leu Gln Ala Leu Leu Leu Ser Ser Asn Gln
865                 870                 875                 880

Glu Leu Gln His Arg Gly Ala Val Val Val Leu Asn Met Val Glu Ala
            885                 890                 895

Ser Arg Glu Ile Ala Ser Thr Leu Met Glu Ser Glu Met Met Glu Ile
            900                 905                 910

Leu Ser Val Leu Ala Lys Gly Asp His Ser Pro Val Thr Arg Ala Ala
        915                 920                 925

Ala Ala Cys Leu Asp Lys Ala Val Glu Tyr Gly Leu Ile Gln Pro Asn
    930                 935                 940

Gln Asp Gly Glu
945

(2) INFORMATION FOR SEQ ID NO:15:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:15:

Asp Tyr Lys Asp Asp Asp Asp Lys
1               5
```